US010456464B2

(12) United States Patent
Shishido et al.

(10) Patent No.: US 10,456,464 B2
(45) Date of Patent: Oct. 29, 2019

(54) LIQUID IMMUNITY INDUCTION-PROMOTING COMPOSITION AND VACCINE PHARMACEUTICAL COMPOSITION THAT INCLUDE THROMBOSIS TREATMENT DRUG

(71) Applicant: NITTO DENKO CORPORATION, Osaka (JP)

(72) Inventors: Takuya Shishido, Osaka (JP); Daisuke Asari, Osaka (JP); Kyohei Matsushita, Osaka (JP); Mitsuhiko Hori, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 15/501,339

(22) PCT Filed: Aug. 4, 2015

(86) PCT No.: PCT/JP2015/072104

§ 371 (c)(1),
(2) Date: Feb. 2, 2017

(87) PCT Pub. No.: WO2016/021602

PCT Pub. Date: Feb. 11, 2016

(65) Prior Publication Data

US 2017/0224812 A1 Aug. 10, 2017

(30) Foreign Application Priority Data

Aug. 4, 2014 (JP) ................................ 2014-159001

(51) Int. Cl.

| | |
|---|---|
| ***A61K 39/39*** | (2006.01) |
| ***A61K 31/235*** | (2006.01) |
| ***A61K 31/4465*** | (2006.01) |
| ***A61K 31/4545*** | (2006.01) |
| ***A61K 31/4709*** | (2006.01) |
| ***A61K 31/5377*** | (2006.01) |
| *A61K 39/00* | (2006.01) |

(52) U.S. Cl.

CPC ............ *A61K 39/39* (2013.01); *A61K 31/235* (2013.01); *A61K 31/4465* (2013.01); *A61K 31/4545* (2013.01); *A61K 31/4709* (2013.01); *A61K 31/5377* (2013.01); *A61K 2039/54* (2013.01); *A61K 2039/542* (2013.01); *A61K 2039/543* (2013.01); *A61K 2039/55511* (2013.01); *A61K 2039/575* (2013.01)

(58) Field of Classification Search

None
See application file for complete search history.

(56) References Cited

U.S. PATENT DOCUMENTS

2014/0193446 A1 7/2014 Lin et al.

FOREIGN PATENT DOCUMENTS

| | | | |
|---|---|---|---|
| CN | 103908662 | A | 7/2014 |
| EP | 2754436 | A1 | 7/2014 |
| FR | 2128467 | A1 | 10/1972 |
| JP | 4428486 | B1 | 3/2010 |
| JP | 2010-132633 | A | 6/2010 |
| WO | 2005/039614 | A2 | 5/2005 |
| WO | 2008/044465 | A1 | 4/2008 |

OTHER PUBLICATIONS

Delafuente et al., “Influenza vaccination and warfarin anticoagulation: a comparison of subcutaneous and intramuscular routes of administration in elderly men”, Pharmacotherapy, 1998, 18(3):631-636.*
Oduah et al. (Pharmaceuticals, 2016, p. 1-12).*
Harenberg et al. (British Journal of Pharmacology, 2012, vol. 165, p. 363-372).*
Soine (Journal of Pharmaceutical Sciences, 1964, vol. 53, p. 231).*
Vacca et al. PLOS, 2016, p. 1-7.*
Serruto et al. (PNAS, 2010, vol. 107, p. 3770-3775).*
Lecoq et al. (Vaccine, 2008, vol. 26, p. 2615-2626).*
European Search Report issued with respect to Application No. 15829891.9, dated Dec. 19, 2017.
Jokay et al., “Effect of Heparin on the Priming with a Protein Antigen in Mice”, Z. Immun.—Forsch., vol. 152, pp. 343-348, 1976.
Lecoq et al., “Increasing the humoral immunogenic properties of the HIV-1 Tat protein using a ligand-stabilizing strategy”, Vaccine, vol. 26, pp. 2615-2626, 2008.
Zhou L. et al., “Plasticity of CD4+ T Cell Lineage Differentiation”, Immunity, 30, 2009, pp. 646-655.
Lipscomb M.F. et al., “Dendritic Cells: Immune Regulators in Health and Disease”, Physiol Rev., vol. 82, 2002, pp. 97-130.
Mazzoni A. et al., “Controlling the Toll road to dendritic cell polarization”, Journal of Leukocyte Biology, vol. 75, 2004, pp. 721-730.
Stevceva L. et al., “Mucosal Adjuvants”, Current Pharmaceutical Design, vol. 11, No. 6, 2005, pp. 801-811.
Millet J. et al., “Antithrombotic and Anticoagulant Activities of a Low Molecular Weight Fucoidan by the Subcutaneous Route”, Thrombosis and Haemostasis, vol. 81, 1999, pp. 391-395.
Delafuente J.C. et al., “Influenza Vaccination and Warfarin Anticoagulation: A Comparison of Subcutaneous and Intramuscular Routes of Administration in Elderly Men”, Pharmacotherapy, vol. 18, No. 3, 1998, pp. 631-636.

(Continued)

*Primary Examiner* — Agnieszka Boesen
(74) *Attorney, Agent, or Firm* — Greenblum & Bernstein, P.L.C.

(57) ABSTRACT

The present invention aims to provide a humoral immunity induction-promoting composition and a vaccine pharmaceutical composition which can universally be used for inducing humoral immunity to various antigens and exert a high antibody production inducing effect. The present invention relates to a vaccine pharmaceutical composition for inducing humoral immunity containing an antigen and a humoral immunity induction promoter whose active ingredient is a thrombosis treatment drug.

7 Claims, 3 Drawing Sheets

(56) References Cited

OTHER PUBLICATIONS

Mizutani S. et al., "Gagome-Yurai fucoidan wo rat ni keiko-touyo suruto kessen-keisei ga yokusei sareta (Oral administration of kjellmaniella crassifolia-derived fucoidan to rat supressed formation of thrombus)", The Japanese Society of Carbonhydrate Research Nenkai Yoshishu, vol. 26, 2006, pp. 12-13.
Negishi H. et al., "Supplementation of Elderly Japanese Men and Women with Fucoidan from Seaweed Increases Immune Responses to Seasonal Influenza Vaccination", The Journal of Nutrition, vol. 143, No. 11, 2013, pp. 1794-1798.
International Search Report issued with respect to Application No. PCT/JP2015/072104, dated Oct. 27, 2015.
International Preliminary Report on Patentability issued with respect to Application No. PCT/JP2015/072104, dated Feb. 7, 2017.
Office Action issued in EP Application No. 15829891.9, dated Aug. 1, 2018.
Office Action for JP App. No. 2015-154346 dated May 7, 2019 (w/ translation).
Office Action for counterpart CN App. No. 201580042066.X dated Jun. 4, 2019 (full translation attached).

* cited by examiner

LIQUID IMMUNITY INDUCTION-PROMOTING COMPOSITION AND VACCINE PHARMACEUTICAL COMPOSITION THAT INCLUDE THROMBOSIS TREATMENT DRUG

TECHNICAL FIELD

The present invention relates to a humoral immunity induction-promoting composition for inducing humoral immunity and a vaccine pharmaceutical composition.

BACKGROUND ART

Common widely used vaccines are made from pathogens (e.g., microorganisms, viruses) or such pathogens whose toxicity is partially weakened or eliminated. The vaccines are administered to living bodies to induce immunity to prevent infectious diseases.

Dendritic cells after having engulfed viruses, microorganisms, or like foreign bodies migrate to lymph nodes and give naive T cells (Th0 cells) the information of the foreign bodies, thus inducing the differentiation of helper T cells. Through the interaction with dendritic cells, Th0 cells differentiate into type 1 helper T cells (Th1 cells), which are responsible for cellular immunity, and type 2 helper T cells (Th2 cells), which are responsible for humoral immunity (see Non-Patent Literature 1 and Non-Patent Literature 2, for example).

Many toll-like receptors (TLRs) are expressed in immunocompetent cells responsible for the innate immunity system, including dendritic cells. They are activated upon receiving a TLR ligand and promote the differentiation of helper T cells, thus activating immune reactions (see Non-Patent Literature 3, for example). For immunity activation, only the reaction routes via TLRs have been known, and other reaction routes have remained unclear.

It is known that immunity activation effects can be given by toxins such as cholera toxin or *Escherichia coli* heat-labile enterotoxin or fat/oil adjuvants that enhance the effects of immune reactions by slow-release of antigens. However, they have problems in terms of the balance between the safety and the efficacy (see Non-Patent Literature 4, for example).

It is also known that a trypsin-like serine protease called thrombin, which is responsible for forming hemostatic plugs or healing of wounds, is involved with immune response and used as an adjuvant for promoting antibody production (see Patent Literature 1, for example).

It is unknown, however, if thrombosis treatment drugs (e.g., anticoagulants that inhibits blood coagulation factors, antiplatelets that inhibits aggregation of platelets) with effects opposite to those of thrombin, which is responsible for thrombus formation, can be effectively used as an adjuvant for promoting antibody production. It is also unknown if direct administration of the thrombosis treatment drug with an antigen to a living body can induce an antigen-specific humoral immune response.

CITATION LIST

Patent Literature

Patent Literature 1: WO 2008/044465

Non Patent Literature

Non-Patent Literature 1: Lipscomb MF. et al., *Physiol Rev.*, 82, 97-130 (2002)

Non-Patent Literature 2: Zhou L. et al., *Immunity*, 30, 646-655 (2009)

Non-Patent Literature 3: Mazzoni A. et al., *J Leukoc Biol.*, 75, 721-730 (2004)

Non-Patent Literature 4: Stevceva L. et al., *Curr Pharm Des*, 11, 801-811 (2005)

SUMMARY OF INVENTION

Technical Problem

The present invention aims to provide a humoral immunity induction-promoting composition and a vaccine pharmaceutical composition which can universally be used for inducing humoral immunity to various antigens and exert a high antibody production inducing effect.

Solution to Problem

The present inventors focused on thrombosis treatment drugs with effects opposite to those of thrombin, such as anticoagulants that inhibit blood coagulation factors or antiplatelets that inhibit activation of platelets. As a result of intensive studies, the inventors found out that, surprisingly, administration of a thrombosis treatment drug such as an anticoagulant or an antiplatelet to a subject together with an antigen leads to induction of an antigen-specific humoral immune response in the subject.

Accordingly, the present invention found out that direct administration of an antigen and a thrombosis treatment drug together or separately to the same site or different sites of a living body enables effective induction of an antigen-specific humoral immune reaction through a reaction not involving a TLR stimulus by a TLR ligand. The thrombosis treatment drugs are approved as medicaments, so that they have the advantage of being highly safe.

Accordingly, the present invention is directed to a humoral immunity induction-promoting composition containing a humoral immunity induction promoter whose active ingredient is a thrombosis treatment drug.

Preferably, the thrombosis treatment drug in the present invention is a thrombogenesis-suppressing compound.

Preferably, the thrombogenesis-suppressing compound is at least one of an anticoagulant or an antiplatelet, the anticoagulant being at least one selected from the group consisting of heparin, dalteparin, fondaparinux, antissasin, TAP (tick anticoagulant peptide), rivaroxaban, apixaban, edoxaban, betrixaban, eribaxaban, YM-150, LY-517717, TAK-442, ximelagatran, dabigatran, argatroban, hirudin, nafamostat, camostat, gabexate, warfarin, and coumarin, the antiplatelet being at least one selected from the group consisting of abciximab, eptifibatide, and tirofiban.

The present invention is also directed to a vaccine pharmaceutical composition for inducing humoral immunity containing an antigen and the humoral immunity induction-promoting composition.

Preferably, the vaccine pharmaceutical composition of the present invention is administered to a body surface.

Preferably, the vaccine pharmaceutical composition of the present invention is administered by intradermal injection, subcutaneous injection, or intramuscular injection.

The present invention will be described in detail below.

The humoral immunity induction-promoting composition and vaccine pharmaceutical composition of the present invention are used for inducing humoral immunity.

The humoral immunity inducing effect may be quantitatively determined by any method. Various methods have been developed. For example, the effect can be determined by an immunity induction experiment using an animal model for immunological evaluation and ELISA (antigen-specific IgG antibody). The sample for ELISA may be, for example, blood of the animal model for immunological evaluation.

The humoral immunity induction-promoting composition of the present invention contains a humoral immunity induction promoter whose active ingredient is a thrombosis treatment drug. Owing to the inclusion of the humoral immunity induction promoter whose active ingredient is a thrombosis treatment drug, the humoral immunity induction-promoting composition of the present invention can effectively induce antigen-specific humoral immunity.

As used herein, the term "humoral immunity induction promoter" means any substance that can improve the efficiency to induce humoral immunity to an antigen administered with the substance, as compared to the efficiency obtained without the substance. The substance is not limited by the mechanism of promoting immunity induction, but the term means those specified herein.

As used herein, the term "thrombosis treatment drug" means a substance that inhibits aggregation of blood-clotting proteins and cells related thereto such as platelets.

As used herein, the "thrombogenesis-suppressing compound" means an anticoagulant that inhibits blood coagulation factors and/or an antiplatelet that inhibits activation of platelets.

As used herein, the term "anticoagulant" means a substance that itself has a function to act on blood coagulation factors or the like to inhibit blood coagulation effects. Examples of the anticoagulant include heparin, dalteparin, fondaparinux, antissasin, tick anticoagulant peptide (TAP), rivaroxaban, apixaban, edoxaban, betrixaban, eribaxaban, YM-150, LY-517717, TAK-442, ximelagatran, dabigatran, argatroban, hirudin, nafamostat, camostat, gabexate, warfarin, coumarin, and derivatives thereof, and pharmacologically acceptable salts thereof.

As used herein, the term "antiplatelet" means a substance that itself has a function to act on platelets to inhibit aggregation of platelets. Examples of the antiplatelet include abciximab, eptifibatide, tirofiban, and derivatives thereof, and pharmacologically acceptable salts thereof.

The "salt" as used herein may be any organic acid salt or inorganic acid salt. The salt is preferably a pharmacologically acceptable salt.

As used herein, the "pharmacologically acceptable salt" means a salt that does not adversely affect the subject and does not eliminate pharmacological activity of the components of the vaccine pharmaceutical composition. Examples of such a salt include inorganic acid salts (e.g., hydrochlorides, phosphates), organic acid salts (e.g., acetates, phthalates, TFA salts, mesylates), metal salts (e.g., alkali metal salts (e.g., sodium salts, potassium salts), alkaline earth metal salts (e.g., calcium salts, magnesium salts, aluminum salts), and amine salts (e.g., triethylamine salts, benzylamine salts, diethanolamine salts, t-butylamine salts, dicyclohexylamine salts, arginine salts, dimethylammonium salts, ammonium salts).

In the humoral immunity induction-promoting composition of the present invention, the amount of the humoral immunity induction promoter whose active ingredient is a thrombosis treatment drug is not limited. The amount is preferably 0.0001 to 100% by weight, more preferably 0.001 to 80% by weight, still more preferably 0.01 to 50% by weight, most preferably 0.05 to 20% by weight based on the total weight of the humoral immunity induction-promoting composition. When the amount is less than 0.0001% by weight, the humoral immunity induction effect may be insufficient. When the amount is more than 100% by weight, the composition may cause safety issues.

The vaccine pharmaceutical composition of the present invention contains an antigen and a humoral immunity induction promoter whose active ingredient is a thrombosis treatment drug.

Owing to the inclusion of the antigen and the humoral immunity induction promoter whose active ingredient is a thrombosis treatment drug, the vaccine pharmaceutical composition of the present invention can effectively induce antigen-specific humoral immunity.

The antigen is preferably an infectious pathogen-derived antigen.

The infectious pathogen-derived antigen refers to any substance that can be a target of an immune response generated by a subject living body. The infectious pathogen-derived antigen may be a substance that can be a target of an immune response (e.g., mature of an immunocompetent T-cell, increase in cytokine production, promotion of antibody production) when coming in contact with an immunocompetent cell. An infectious disease can be addressed (for example, treated and/or prevented) by administrating the infectious disease-derived antigen and the composition for promoting humoral immunity induction together to a subject using the vaccine pharmaceutical composition of the present invention.

The infectious pathogen-derived antigen is not limited as long as it is an infectious pathogen or an antigen derived from an infectious pathogen.

The diseases caused by the infectious pathogens are not limited. Examples thereof include virus diseases caused by infection with viruses such as adenovirus (e.g., human adenovirus), herpesvirus (e.g., herpes simplex virus, varicella-zoster virus, cytomegalovirus, human herpesvirus, Kaposi sarcoma-associated herpesvirus), picornavirus (e.g., poliovirus, common cold virus, hepatitis A virus), poxvirus (e.g., smallpox virus, vaccinia virus, molluscum contagiosum virus), picornavirus (e.g., rhinovirus, enterovirus), orthomyxovirus (e.g., influenza virus), paramyxovirus (e.g., parainfluenza virus, mumps virus, measles virus, respiratory syncytial virus (RSV), Newcastle disease virus), parvovirus (e.g., adeno associated virus), togavirus (e.g., rubella virus), coronavirus (e.g., SARS coronavirus), hepadnavirus (e.g., hepatitis B virus), flavivirus (e.g., Japanese encephalitis virus, yellow fever virus, dengue virus, West Nile fever virus, St. Louis encephalitis virus, Murray Valley encephalitis virus, hepatitis C virus, hepatitis G virus), hepevirus (e.g., hepatitis E virus), papillomavirus (e.g., human papilloma virus), calicivirus (e.g., norovirus), rhabdovirus (e.g., rabies virus, vesicular stomatitis virus), filovirus (e.g., Ebola hemorrhagic fever virus), arenavirus (e.g., Lassa virus, hepatitis D virus), bunyavirus (e.g., California encephalitis virus, Rift Valley fever virus), reovirus (e.g., rotavirus), or retrovirus (e.g., human immunodeficiency virus (HIV), adult T-cell leukemia virus); bacterial diseases such as those caused by infection with a bacterium such as *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococci, Neisseria, Clostridium, Bacillus, Corynebacterium, Mycobacterium, Campyrobacter, Vibrio, Serratia, Providencia, Chromobacterium, Brucella, Yersinia, Haemophilus*, or *Bordetella*; fungous diseases such as chlamydia, candidiasis, aspergillosis, histoplasmosis, and cryptococcal meningitis; malaria; pneumocystis carinii pneumonia; leishmaniasis; cryptosporidiosis; toxoplasmosis; and Trypanosoma infection.

In one preferred embodiment, humoral immunity is effectively induced by administrating the vaccine composition containing an antigen and a humoral immunity induction promoter whose active ingredient is a thrombosis treatment drug.

In one preferred embodiment, humoral immunity is effectively induced by administrating the vaccine pharmaceutical composition containing an antigen and a humoral immunity induction promoter whose active ingredient is a thrombosis treatment drug that is an anticoagulant and/or an antiplatelet.

The amount of the antigen in the vaccine pharmaceutical composition of the present invention is not limited, but is preferably 0.000001 to 50% by weight, more preferably 0.00001 to 20% by weight based on the total weight of the composition.

The amount of the humoral immunity induction promoter whose active ingredient is a thrombosis treatment drug in the vaccine pharmaceutical composition of the present invention is not limited, but is preferably 0.001 to 10,000 parts by weight, more preferably 0.01 to 10,000 parts by weight based on 1 part by weight of the antigen.

If the amount of the immunity induction promoter is less than the lower limit, i.e., 0.001 parts by weight, the immunity induction effect may be insufficient. If the amount of the immunity induction promoter is more than the upper limit, i.e., 10,000 parts by weight, safety issues may arise.

The vaccine pharmaceutical composition of the present invention may contain additive(s), if necessary. The additives can be selected depending on, for example, the main components of the base, the compatibility with the antigen and the humoral immunity induction promoter whose active ingredient is a thrombosis treatment drug, or intended administration regimen. Examples of the additives include isotonizing agents, antiseptics, antioxidants, resolvents, solubilizing agents, suspending agents, fillers, pH adjusters, stabilizers, absorption promoters, release-rate controlling agents, colorants, plasticizers, crosslinking agents, and adhesives. These additives may be used alone or in combination of two or more thereof.

Although the vaccine pharmaceutical composition of the present invention may be intradermally, subcutaneously, or intramuscularly administered, they are preferably administered to the body surface, more preferably transdermally or transmucosally administered. Accordingly, the vaccine pharmaceutical composition of the present invention may be a vaccine pharmaceutical composition for intradermal, subcutaneous, or intramuscular administration, but is preferably a vaccine pharmaceutical composition for transdermal administration or transmucosal administration. The transdermal administration may be non-invasive or minimally invasive. The transdermal administration or transmucosal administration of the vaccine pharmaceutical composition of the present invention to a subject enables effective induction of antigen-specific humoral immunity.

As used herein, the term “subject” means any animal to which the vaccine pharmaceutical composition at a practical stage can be administered so as to induce an immune response. The term typically means mammals including human (e.g., mouse, rat, canine, feline, leporine, equine, bovine, ovine, porcine, caprine, simian, and chimpanzee). The subject is particularly preferably a human.

<Vaccine Pharmaceutical Composition for Transmucosal Administration>

The transmucosal administration may be, for example, sublingual administration, transnasal administration, buccal administration, rectal administration, and vaginal administration.

Examples of the dosage form of the vaccine pharmaceutical composition for transmucosal administration include semisolid formulations such as gels (jellies), creams, ointments, and plasters; solutions; solid formulations such as powders, fine granules, granules, films, tablets, and orally disintegrating tablets (freeze dry type); mucosal sprays such as aerosols, and inhalants. The categories, definition, characteristics, production processes, and the like of these compositions are well known in the art. See the Japanese Pharmacopoeia 16th edition, for example. Preferred among the dosage forms are solutions and solid formulations (e.g., orally disintegrating tablets (freeze dry type), films). The materials for these are not limited, and conventionally known materials can be used.

In the vaccine pharmaceutical composition for mucosal administration, the amounts of the antigen and the humoral immunity induction promoter whose active ingredient is a thrombosis treatment drug are not limited, and comply with those in the vaccine pharmaceutical composition of the present invention.

Examples of the solvent used for the solutions include an appropriate amount of water, ethanol, glycerin, and propylene glycol. A solution can be prepared by dispersing or dissolving the ingredients (i.e., the antigen, the humoral immunity induction promoter whose active ingredient is a thrombosis treatment drug, and if necessary, the second humoral immunity induction promoter and the like) into the solvent.

Any base may be used for the gels (jellies). Examples thereof include hydrogel bases, such as carboxyvinyl polymers, gel bases, fat-free ointment, polyvinylpyrrolidone, polyvinyl alcohol, sodium polyacrylate, carboxymethylcellulose, starch, xanthan gum, karaya gum, sodium alginate, methylcellulose, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, carboxyvinyl polymers, tragacanth, gum arabic, tara gum, tamarind seed gum, psyllium seed gum, agar, gellan gum, glucomannan, locust bean gum, guar gum, carrageenan, dextrin, dextran, amylose, potassium carboxymethylcellulose, sodium carboxymethylcellulose, calcium carboxymethylcellulose, pullulan, chitosan, sodium carboxymethyl starch, Plantago testa, galactomannan, Eudragit, casein, alkyl alginate, gelatin, and polyethylene glycol. A fluid gel or a gel with formability can be prepared by dissolving any of these bases into a solvent and adding the ingredients. The solvent is preferably water, but glycerin, propylene glycol, or the like can also be used.

Examples of the base used for the creams include water/oil-type bases such as hydrophilic ointment and vanishing cream; and oil/water-type bases such as hydrophilic Vaseline, purified lanolin, Aquahole, Eucerin, Neocerin, hydrous lanolin, cold cream, hydrophilic plastibase. A cream can be prepared by placing any of these bases into a fat/oil solvent or water and stirring the mixture at a high speed with, for example, a homogenizer.

Any base may be used for the films. Examples thereof include polyvinylpyrrolidone, polyvinyl alcohol, sodium polyacrylate, carboxymethylcellulose, starch, xanthan gum, karaya gum, sodium alginate, methylcellulose, carboxyvinyl polymers, agar, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, carboxyvinyl polymers, tragacanth, gum arabic, locust bean gum, guar gum, carrageenan, dextrin, dextran, amylose, potassium carboxymethylcellulose, sodium carboxymethylcellulose, calcium carboxymethylcellulose, pullulan, chitosan, sodium carboxymethyl starch, Plantago testa, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate-methacrylic acid-methyl methacrylate copolymer, ethyl acrylate-methyl methacrylate copolymer, polyvinyl acetal diethylamino acetate, casein, and alkyl alginate. A film can be prepared by dissolving any of these bases in a polar organic solvent such as water or ethanol, adding the ingredients, applying the solution to form a thin film, and drying the film.

Any additives can be used for the powders, fine granules, granules, or tablets. Examples thereof include excipients such as lactose, corn starch, and crystalline cellulose, and binders such as hydroxypropylcellulose and gum arabic. Powder, fine granules, granules, and tablets can be prepared by adding these additives to an appropriate amount of solvent such as water or ethanol, adding the ingredients, mixing and stirring them, and then subjecting the resulting mixture to a combination of processes such as granulation, drying, and tablet compression. If necessary, a lubricant such as magnesium stearate and a coating agent such as hydroxypropylcellulose or sucrose may be added.

Any base may be used for the orally disintegrating tablets (freeze dry type). Examples thereof include polysaccharides such as gelatin and pullulan, and hydrogel bases such as hydroxypropylcellulose. Forming aids such as mannitol, trehalose, sorbitol, or glycine may also be used. An orally disintegrating tablet (freeze dry type) can be prepared by dissolving any of these bases and a forming aid in water, adding the ingredients, dispensing the resulting solution, and then freeze drying the solution.

The content of the aerosol may be, for example, a solution, a highly fluidic gel, a cream, or fine powder such as a powdered drug. Dispersing the content as solid or liquid microparticles in a gas using a spray device enables effective administration to an administration site such as the oral mucosa or the nasal mucosa.

<Humoral Immunity Induction-Promoting Composition for Transmucosal Administration>

The humoral immunity induction-promoting composition for transmucosal administration according to the present invention allows, in mucosal administration of a humoral immunity induction promoter whose active ingredient is a thrombosis treatment drug to the subject, more effective exertion of immunity induced by various antigens administered together with or separately from the humoral immunity induction promoter.

The administration route and the formulation of the humoral immunity induction-promoting composition for transmucosal administration can be the same as those of the vaccine pharmaceutical composition for transmucosal administration. The formulation of the humoral immunity induction-promoting composition for transmucosal administration can be prepared with the same materials as those used for preparing the formulation of the vaccine pharmaceutical composition for transmucosal administration.

<Vaccine Pharmaceutical Composition for Transdermal Administration>

Examples of the dosage form of the vaccine pharmaceutical composition for transdermal administration include solutions for external use such as liniments and lotions; sprays for external use such as aerosols; patches such as gels, tapes, poultices; ointments; plasters; and creams. The categories, definition, characteristics, production processes, and the like of these compositions are well known in the art. See the Japanese Pharmacopoeia 16th edition, for example. The materials for these are not limited, and conventionally known materials can be used.

Preferred among these dosage forms are creams and patches (e.g., tapes, poultices).

In the vaccine pharmaceutical composition for transdermal administration, the amounts of the antigen and the humoral immunity induction promoter whose active ingredient is a thrombosis treatment drug are not limited, and comply with those in the vaccine pharmaceutical composition of the present invention.

Examples of the base used for the liniments include water, ethanol, fatty oils, hard paraffin, soft paraffin, liquid paraffin, glycerin, paraffin oil, beeswax, metallic soap, mucilage, natural oils (e.g., almond oil, corn oil, peanut oil, castor oil, olive oil, and derivatives thereof (e.g., polyoxyl castor oil)), mutton tallow or derivatives thereof, and fatty acids and/or fatty acid esters (e.g., stearic acid, oleic acid, isopropyl myristate).

Lotion is a formulation containing the ingredients finely and homogenously dispersed in an aqueous liquid and includes suspension lotion and emulsion lotion. The suspending agent may be, for example, gum arabic, sodium alginate, sodium carboxymethylcellulose, methylcellulose, or bentonite. The emulsifier may be, for example, sodium lauryl sulfate or sorbitan fatty acid ester.

Examples of the base used for the ointments include common hydrophobic bases such as fats and oils, waxes, and hydrocarbon compounds. Specific examples include mineral bases such as yellow Vaseline, white Vaseline, paraffin, liquid paraffin, plastibase, and silicone, and animal or vegetable bases such as beeswax and animal or vegetable oils and fats.

Examples of the base used for the creams include water/oil type bases such as hydrophilic ointment and vanishing cream; and oil/water type bases such as hydrophilic Vaseline, purified lanolin, Aquahole, Eucerin, Neocerin, hydrous lanolin, cold cream, and hydrophilic plastibase.

Any base may be used for the gels. Examples thereof include hydrogel bases such as carboxyvinyl polymers, gel bases, fat-free ointment, polyvinylpyrrolidone, polyvinyl alcohol, sodium polyacrylate, carboxymethylcellulose, starch, xanthan gum, karaya gum, sodium alginate, methylcellulose, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, carboxyvinyl polymer, tragacanth, gum arabic, tara gum, tamarind seed gum, psyllium seed gum, agar, gellan gum, glucomannan, locust bean gum, guar gum, carrageenan, dextrin, dextran, amylose, potassium carboxymethylcellulose, sodium carboxymethylcellulose, calcium carboxymethylcellulose, pullulan, chitosan, sodium carboxymethyl starch, Plantago testa, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate-methacrylic acid-methyl methacrylate copolymer, ethyl acrylate-methyl methacrylate copolymer, polyvinyl acetal diethylamino acetate, casein, alkyl alginate, gelatin, and polyethylene glycol.

Any base may be used for the poultices. Examples thereof include gelatin, sodium carboxymethylcellulose, methylcellulose, sodium polyacrylate, kaolin, polyvinyl alcohol, polyvinylpyrrolidone, glycerin, propylene glycol, and water.

The tape preferably includes an adhesive layer containing ingredients (i.e., the antigen, the humoral immunity induction promoter whose active ingredient is a thrombosis treatment drug, and if necessary, the second humoral immunity induction promoter and the like) and a support that supports the adhesive layer. The tape may include a release liner that prevents exposure of the adhesive layer before use and can be easily removed at the time of use.

The adhesive forming the adhesive layer is not limited. Examples thereof include acrylic adhesives containing acrylic polymers; rubber adhesives containing rubber elastomers; silicone adhesives such as silicone rubber, dimethyl siloxane-based adhesives, and diphenyl siloxane-based adhesives; vinyl ether adhesives such as polyvinyl methyl ether, polyvinyl ethyl ether, and polyvinyl isobutyl ether; vinyl ester adhesives such as vinyl acetate-ethylene copolymer; and polyester adhesives containing a carboxylic acid component (e.g., dimethyl terephthalate, dimethyl isophthalate, dimethyl phthalate) and a polyalcohol component (e.g., ethylene glycol). Particularly preferred adhesives are acrylic adhesives, rubber adhesives, and silicone adhesives. For good antigen dispersibility/releasability, hydrophilic bases such as sodium polyacrylate are preferred.

The amount of the adhesive in the adhesive layer is not limited, but is preferably 10 to 90% by weight, more preferably to 80% by weight in terms of solids based on the total weight of the adhesive layer.

The acrylic adhesive is preferably mainly composed of a polymer which contains alkyl (meth)acrylate as a first monomer.

Examples of the first monomer include (meth)alkyl acrylate having a C1-C18 linear, branched, or cyclic alkyl group. In particular, alkyl (meth)acrylate having a C4-C18 linear, branched, or cyclic alkyl group are preferred. Moreover, alkyl (meth)acrylates having a C4-C8 linear, branched, or cyclic alkyl group (e.g., butyl, pentyl, hexyl, cyclohexyl, heptyl, octyl, or 2-ethylhexyl, preferably butyl, 2-ethylhexyl, or cyclohexyl, particularly preferably 2-ethylhexyl) are more preferred because the use of a monomer component that lowers the glass transition temperature of the polymer is more suitable for providing adhesiveness at normal temperature.

Specifically, butyl acrylate, 2-ethylhexyl acrylate, 2-ethylhexyl methacrylate, cyclohexyl acrylate, and cyclohexyl methacrylate are preferred as the first monomer, with 2-ethylhexyl acrylate being particularly preferred. These first monomers can be used alone or in combination of two or more thereof.

The first monomer may be copolymerized with a second monomer. Examples of the second monomer include monomers having a functional group that can be a crosslinking point when a crosslinking agent is used. Examples of such a functional group that can be involved with crosslinking reaction include a hydroxy group, a carboxy group, and a vinyl group, with a hydroxy group and a carboxy group being preferred.

Specific examples of the second monomer include hydroxyethyl (meth)acrylate, hydroxypropyl (meth)acrylate, N-hydroxyalkyl(meth)acrylamide, (meth)acrylic acid, itaconic acid, maleic acid, maleic anhydride, mesaconic acid, citraconic acid, and glutaconic acid. From the viewpoint of availability, acrylic acid, methacrylic acid, and hydroxyethyl acrylate (in particular, 2-hydroxyethyl acrylate) are preferred, with acrylic acid being most preferred. These second monomers may be used alone or in combination of two or more thereof.

The first and second monomer may be further copolymerized with a third monomer.

Examples of the third monomer include vinyl esters such as vinyl acetate and vinyl propionate; vinyl ethers such as methyl vinyl ether and ethyl vinyl ether; vinylamides such as N-vinyl-2-pyrrolidone and N-vinylcaprolactam; alkoxy (meth)acrylates such as methoxyethyl (meth)acrylate, ethoxyethyl (meth)acrylate, and tetrahydrofurfuryl (meth) acrylate; hydroxy group-containing monomers (as the third monomer, not as a crosslinking point) such as hydroxypropyl (meth)acrylate and α-hydroxymethyl acrylate; (meth) acrylic acid derivatives having an amide group such as (meth)acrylamide, dimethyl(meth)acrylamide, N-butyl (meth)acrylamide, and N-methylol(meth)acrylamide; aminoalkyl (meth)acrylates such as aminoethyl (meth)acrylate, dimethylaminoethyl (meth)acrylate, and t-butylaminoethyl (meth)acrylate; alkoxyalkylene glycol (meth)acrylates such as methoxyethylene glycol (meth)acrylate, methoxydiethylene glycol (meth)acrylate, methoxypolyethylene glycol (meth)acrylate, and methoxypolypropylene glycol (meth)acrylate; (meth)acrylonitrile; monomers having a sulfonic acid such as styrenesulfonic acid, allylsulfonic acid, sulfopropyl (meth)acrylate, (meth)acryloyloxynaphthalenesulfonic acid, and acrylamidemethylsulfonic acid; and vinyl group-containing monomers such as vinylpiperidone, vinylpyrimidine, vinylpiperazine, vinylpyrrole, vinylimidazole, vinyloxazole, and vinylmorpholine. Preferred among these are vinyl esters, and vinylamides. A preferred vinyl ester is vinyl acetate, and a preferred vinylamide is N-vinyl-2-pyrrolidone. These third monomers can be use alone or in combination of two or more thereof.

When the acrylic adhesive is a copolymer of alkyl (meth) acrylate (first monomer) and a vinyl monomer (second monomer) having a functional group that can be involved with crosslinking reaction, the weight ratio between the alkyl (meth)acrylate and the vinyl monomer having a functional group that can be involved with crosslinking reaction is preferably 99 to 85:1 to 15, more preferably 99 to 90:1 to 10.

When the acrylic adhesive is a copolymer of alkyl (meth) acrylate (first monomer), a vinyl monomer (second monomer) having a functional group that can be involved with crosslinking reaction, and a different monomer (third monomer), the weight ratio between the alkyl (meth)acrylate, the vinyl monomer having a functional group that can be involved with crosslinking reaction, and the different monomer is preferably 40 to 94:1 to 15:5 to 50, more preferably 50 to 89:1 to 10:10 to 40.

The polymerization reaction is not limited, and may be performed by a known method per se. For example, the above monomers are reacted in the presence of a polymerization initiator (e.g., benzoyl peroxide, azobisisobutyronitrile) in a solvent (e.g., ethyl acetate) at 50° C. to 70° C. for 5 to 48 hours.

The acrylic adhesives more preferably contains any of 2-ethylhexyl acrylate/acrylic acid/N-vinyl-2-pyrrolidone copolymer, 2-ethylhexyl acrylate/N-(2-hydroxyethyl)acrylamide/N-vinyl-2-pyrrolidone copolymer, 2-ethylhexyl acrylate/2-hydroxyethyl acrylate/vinyl acetate copolymer, and 2-ethylhexyl acrylate/acrylic acid copolymer, particularly preferably contains 2-ethylhexyl acrylate/acrylic acid/N-vinyl-2-pyrrolidone copolymer.

The acrylic adhesives may be subjected to physical crosslinking by radiation such as UV irradiation or electron beam irradiation, or may be subjected to chemical crosslinking using crosslinking agents such as an isocyanate compound (e.g., trifunctional isocyanate), an organic peroxide, an organic metal salt, a metal alcoholate, a metal chelate compound, or a multifunctional compound (e.g., a multifunctional external crosslinking agent, a multifunctional monomer for internal crosslinking such as di(meth)acrylate).

Examples of the rubber elastomer forming the rubber adhesive include polyisobutylene-polybutene elastomer, styrene-diene-styrene block copolymer, styrene-butadiene elastomer, nitrile elastomer, chloroprene elastomer, vinylpyridine elastomer, polyisobutylene elastomer, butyl elastomer, and isoprene-isobutylene elastomer. In particular, from the viewpoint of the solubility to the ingredients and the adhesiveness to the skin, preferred elastomers are polyisobutylene (PIB) and styrene-diene-styrene block copolymers (e.g., styrene-butadiene-styrene block copolymer (SBS), styrene-isoprene-styrene block copolymer (SIS)). These rubber elastomers may be used alone or in combination of two or more thereof.

In order to obtain suitable adhesion and suitable solubility to the ingredients, the rubber adhesive may contain a mixture of rubber elastomers that are the same as or different in the components and different in the average molecular weight. For example, preferred is a mixture of a high-molecular-weight polyisobutylene with an average molecular weight of 150,000 to 5,500,000, a medium-molecular-weight polyisobutylene with an average molecular weight of 10,000 to 150,000, and/or a low-molecular-weight polyisobutylene with an average molecular weight of 500 to 4,000. In the mixture, the amount of the high-molecular-weight polyisobutylene is 10 to 80% by weight, preferably 20 to 70% by weight based on the total amount of the polyisobutylenes. The amount of the medium-molecular weight polyisobutylene is 0 to 90% by weight, preferably 10 to 80% by weight based on the total amount of the polyisobutylenes. The amount of the low-molecular-weight polyisobutylene is 0 to 80% by weight, preferably 10 to 60% by weight based on the total amount of the polyisobutylenes.

The "average molecular weight" as used herein means the viscosity average molecular weight calculated by Flory's viscosity equation. The average molecular weight is determined by calculating Staudinger index ($J_0$) from the flow time at 20° C. of the capillary 1 of an Ubbelohde viscometer by Schulz-Blaschke equation and calculating the viscosity average molecular weight using the $J_0$ value according to the formula below.

$$J_0=\eta_{sp}/c(1+0.31\eta_{sp}) \quad \text{(Schulz-Blaschke equation)}$$

$$\eta_{sp}=t/t_0-1$$

t: Flow time of solution (according to Hagenbach-couette correction formula)

$t_0$: Flow time of solvent (according to Hagenbach-couette correction formula)

c: Concentration of solution (g/cm$^3$)

$$J_0=3.06\times10^{-2}\overline{Mv}^{0.65}$$

$\overline{Mv}$: Viscosity average molecular weight

In order to provide suitable tackiness, the rubber adhesive may contain a tackifier, such as rosin resin, polyterpene resin, coumarone-indene resin, petroleum resin, terpene-phenol resin, xylene resin, or alicyclic saturated hydrocarbon resin. These tackifiers may be used alone or in combination of two or more thereof.

The tackifier content is preferably 50% by weight or less, preferably 5 to 40% by weight based on the total weight of the rubber adhesive.

Examples of the silicone adhesives include polyorganosiloxane adhesives, polydimethylsiloxane adhesives, and polydimethyldiphenyl-siloxane adhesives. In particular, commercially available silicone adhesives, such as BIO PSA from Dow Corning Corporation, are preferred.

The adhesive layer may further contain a skin permeation enhancer.

As used herein, the term "skin permeation enhancer" refers to a substance that can improve the efficiency at which a transdermally administered antigen permeates the skin.

The skin permeation enhancer is preferably liquid, that is, fluidic, at room temperature (25° C.). When a mixture of two or more skin permeation enhancers is used, the resulting mixture is preferably liquid at room temperature (25° C.) and has a skin permeation promoting effect. Such an organic liquid component is preferably a hydrophobic liquid component from the viewpoint of the compatibility in the adhesive layer.

Examples of the skin permeation enhancer include higher alcohols, fatty acid esters, and polyalcohol fatty acid esters.

Preferred among the higher alcohols are C8-C18 higher alcohols, and more preferred are C8-C14 higher alcohols. Preferred among the fatty acid esters are fatty acid esters of C8-C18 fatty acids with C1-C18 monohydric alcohols, and more preferred are fatty acid esters of C12-C16 fatty acids with C1-C18 monohydric alcohols. In particular, fatty acid esters are preferred, and isopropyl myristate, isopropyl palmitate, and diethyl sebacate are particularly preferred.

Specific examples of the skin permeation enhancer include higher alcohols such as oleyl alcohol and octyl dodecanol; polyalcohols such as glycerin, ethylene glycol, and polypropylene glycol; higher fatty acids such as oleic acid and caplyric acid; fatty acid esters such as isopropyl myristate, isopropyl palmitate, and ethyl oleate; polybasic acid esters such as diethyl sebacate and diisopropyl adipate; polyalcohol fatty acid esters such as diglyceryl triisostearate, sorbitan monooleate, propylene glycol dicaprylate, polyethylene glycol monolaurate, and polyoxyethyelene sorbitol tetraoleate; polyoxyethylene alkyl ether such as polyoxyethylene lauryl ether; hydrocarbons such as squalane and liquid paraffin; vegetable oils such as olive oil and castor oil; silicone oil; pyrrolidones such as N-methylpyrrolidone and N-dodecylpyrrolidone; and sulfoxides such as decylmethylsulfoxide. These can be used alone or in combination of two or more thereof.

When the rubber or acrylic adhesive is used, the skin permeation enhancer may be polyvinylpyrrolidone, crospovidone, polypropylene glycol, polyvinyl alcohol, carboxyvinyl polymer, hydroxypropylcellulose, or a mixture thereof. In particular, polyvinylpyrrolidone, crospovidone, and polypropylene glycol are preferred.

The amount of the skin permeation enhancer in the adhesive layer is not limited, but is preferably 0.1 to 70% by weight, more preferably 1 to 65% by weight, still more preferably 5 to 60% by weight based on the total weight of the adhesive layer. When the amount of the skin permeation enhancer is 0.1% by weight or more, a high skin permeation promoting effect can be obtained. When the amount of the skin permeation enhancer is 70% by weight or less, a high skin permeation promoting effect can be obtained while reduction in the adhesion and cohesion of the entire adhesive layer can be suppressed.

The thickness of the adhesive layer is not limited, but is preferably 10 to 1000 μm. With the thickness being in the range, the adhesive layer can easily contain the ingredients in effective amounts, easily exhibit sufficient adhesion, and be easily formed.

The support is not limited. Preferably, the support is one substantially impermeable to the ingredients, that is, one that prevents reduction in the amounts of the antigen, the humoral immunity induction promoter whose active ingredient is a thrombosis treatment drug, and if necessary the second humoral immunity induction promoter in the adhesive layer by not allowing them to pass through the support and escape from the back side.

The support may be, for example, a single film containing polyester, polyamide, polyvinylidene chloride, polyethylene, polypropylene, polyvinyl chloride, ethylene-ethyl acrylate copolymer, polytetrafluoroethylene, ionomer resin, or metallic foil or may be a laminated film containing such films. In particular, to improve adhesiveness (anchoring properties) between the support and the adhesive layer, the support is preferably a laminated film including a nonporous plastic film and a porous film each containing any of the above materials. In this case, the adhesive layer is preferably formed on the porous film-side.

The porous film may be any porous film that improves the anchoring properties between the support and the adhesive layer. Examples thereof include paper, woven fabrics, nonwoven fabrics, knitted fabrics, and mechanically perforated sheets. Preferred among these are paper, woven fabrics, and nonwoven fabrics from the viewpoint of the handleability. The porous film preferably has a thickness of 1 to 200 μm from the viewpoint of improving the anchoring properties and also from the viewpoint of the flexibility and attachment operability of the tape. When the porous film is a woven fabric or a nonwoven fabric, the weight per unit area thereof is preferably 5 to 30 $g/m^2$, more preferably 6 to 15 $g/m^2$.

The support is preferably a laminated film including a polyester film (preferably, polyethylene terephthalate film) with a thickness of 1.5 to 6 μm and a polyester (preferably, polyethylene terephthalate) nonwoven fabric with a weight per unit area of 6 to 15 $g/m^2$.

Any release liner can be used as long as it is release-treated and can be peeled with sufficiently light force. For example, the release liner may be a film formed of polyester, polyvinyl chloride, polyvinylidene chloride, or polyethylene terephthalate, paper such as woodfree paper or glassine, or a laminated film including woodfree paper or glassine and a polyolefin, which are release-treated by applying silicone resin, fluororesin, or the like to the side to be in contact with the adhesive layer.

The release liner has a thickness of preferably 10 to 200 μm, more preferably 25 to 100 μm. From the viewpoint of barrier properties and the price, the release liner is preferably formed of a polyester (in particular, polyethylene terephthalate) resin. In this case, from the viewpoint of the handleability, the thickness of the release liner is preferably about 25 to 100 μm.

<Humoral Immunity Induction-Promoting Composition for Transdermal Administration>

The humoral immunity induction-promoting composition for transdermal administration according to the present invention allows, in transdermal administration of a humoral immunity induction promoter whose active ingredient is a thrombosis treatment drug, more effective exertion of humoral immunity induced by various antigens administered together with or separately from the humoral immunity induction promoter.

The formulation of the humoral immunity induction-promoting composition for transdermal administration may be the same as that of the vaccine pharmaceutical composition for transdermal administration. The formulation of the humoral immunity induction-promoting composition for transdermal administration can be prepared with the same materials as those used for preparing the vaccine pharmaceutical composition for transdermal administration.

<Vaccine Pharmaceutical Composition for Intradermal, Subcutaneous, or Intramuscular Administration>

The dosage form of the vaccine pharmaceutical composition for intradermal, subcutaneous, or intramuscular administration is one that has a certain degree of fluidity that allows administration by injection, such as a solution, an aqueous or hydrophobic suspension, or a cream. The categories, definition, characteristics, production processes, and the like of these compositions are well known in the art. See the Japanese Pharmacopoeia 16th edition, for example. The materials for these are not limited, and conventionally known materials can be used.

In the vaccine pharmaceutical composition for intradermal, subcutaneous, or intramuscular administration, the amounts of the antigen and the humoral immunity induction promoter whose active ingredient is a thrombosis treatment drug are not limited, and comply with those in the vaccine pharmaceutical composition of the present invention.

The solvent for the solution may be, for example, an appropriate amount water or saline, ethanol, glycerin, or propylene glycol. A solution can be prepared by dispersing or dissolving the ingredients into the solvent.

Any base may be used for the aqueous suspension include hydrogel bases, such as carboxyvinyl polymers, gel bases, fat-free ointment, polyvinylpyrrolidone, polyvinyl alcohol, sodium polyacrylate, carboxymethylcellulose, starch, xanthan gum, karaya gum, sodium alginate, methylcellulose, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, carboxyvinyl polymers, tragacanth, gum arabic, tara gum, tamarind seed gum, psyllium seed gum, agar, gellan gum, glucomannan, locust bean gum, guar gum, carrageenan, dextrin, dextran, amylose, potassium carboxymethylcellulose, sodium carboxymethylcellulose, calcium carboxymethylcellulose, pullulan, chitosan, sodium carboxymethyl starch, Plantago testa, galactomannan, Eudragit, casein, alkyl alginate, gelatin, and polyethylene glycol. A fluidic suspension can be prepared by dissolving any of these bases into a solvent and adding the ingredients. The solvent is preferably saline, but glycerin, propylene glycol, or the like can also be used.

Any base may be used for the hydrophobic suspension. Examples thereof include water/oil-type bases such as hydrophilic ointment and vanishing cream; and oil/water-type bases such as hydrophilic Vaseline, purified lanolin, Aquahole, Eucerin, Neocerin, hydrous lanolin, cold cream, and hydrophilic plastibase. A fat/oil suspension can be prepared by placing any of these bases into a fat/oil solvent or water, stirring the mixture at a high speed with, for example, a homogenizer, and adding the ingredients.

<Humoral Immunity Induction-Promoting Composition for Intradermal, Subcutaneous, or Intramuscular Administration>

The humoral immunity induction-promoting composition for intradermal, subcutaneous, or intramuscular administration according to the present invention allows, in intradermal, subcutaneous, or intramuscular administration of a humoral immunity induction promoter whose active ingredient is a thrombosis treatment drug to the subject, more effective exertion of humoral immunity induced by various antigens administered together with or separately from the humoral immunity induction promoter.

The formulation of the humoral immunity induction-promoting composition for intradermal, subcutaneous, or intramuscular administration may be the same as that of the vaccine pharmaceutical composition for intradermal, subcutaneous, or intramuscular administration. The formulation of the humoral immunity induction-promoting composition for intradermal, subcutaneous, or intramuscular administration can be prepared with the same materials as those used for preparing the formulation of the vaccine pharmaceutical composition for intradermal, subcutaneous, or intramuscular administration.

When the vaccine pharmaceutical composition of the present invention is administered to the subject, the therapeutically effective amount thereof may widely vary depending on severity of the disease, age and relative health of the subject and other known factors. Generally, satisfactory results can be obtained at a dose of about 0.1 μg to 1 g/kg body weight per day. The humoral immunity induction promoter whose active ingredient is a thrombosis treatment drug is simultaneously or sequentially, preferably simultaneously, administered with the antigen.

When the humoral immunity induction-promoting composition of the present invention is administered to the subject, and when the vaccine pharmaceutical composition containing the humoral immunity induction-promoting composition is administered to the subject, the therapeutically effective amount of the humoral immunity induction promoter whose active ingredient is a thrombosis treatment drug may widely vary depending on factors such as the specific thrombosis treatment drug used or the presence or absence of other humoral immunity induction promoter(s). Generally, satisfactory results can be obtained at a dose of about 0.01 μg to 1 g/kg body weight per day.

The daily dose may be administered in one time, or may be divided into multiple doses (i.e., two or more doses, for example, 2, 3, 4, or 5 doses). The period of continuous administration per dose is preferably appropriately selected in the range from 1 minute to 7 days. The administration interval is preferably appropriately selected from once daily to yearly (e.g., once a day, once every two days, once every three days, once a week, once every two weeks, once a month, once every three months, once every six months, once a year) or longer administration intervals, depending on, for example, the condition of the patient, the severity of the disease, or whether it is for therapeutic purposes or preventive purposes. Generally, for therapeutic purposes for patients actually having a severe disease, the vaccine pharmaceutical composition of the present invention is preferably administered with a higher frequency and/or with a higher dose. For preventive purposes for patients not having a disease, the vaccine pharmaceutical composition of the present invention is preferably administered with a lower frequency and/or with a lower dose.

Advantageous Effects of Invention

The humoral immunity induction-promoting composition and vaccine pharmaceutical composition of the present invention can be non-invasively administered (e.g., transdermally or transmucosally administered) to the body surface or minimally invasively administered to the skin surface (e.g., to the surface of the skin after a corneum removal treatment such as tape stripping or after a corneum perforation treatment such as a microneedle treatment or electroporation), therefore leading to excellent compliance. In other words, problems concerned with QOL of patients, such as pain, fear, injection scars with subsequent cicatrization, or regular hospital visits putting a burden to patients in the case of repetitive administrations, can be reduced. Moreover, as the compositions are easy to administer, patients can administer the compositions by themselves, reducing the risk of infections of health care workers via needle stick injury. Furthermore, medical wastes requiring specific waste treatment, such as injection needles, are not generated.

The humoral immunity induction-promoting composition and vaccine pharmaceutical composition of the present invention in a patch form, such as a tape or a poultice, are advantageous in that they enables secure administration of a predetermined dose and the control of the drug releasing rate at any rate, and that they do not attach to unintended sites when administered. The compositions in a patch form are advantageous also in that since a patch is easily removed, patients can immediately stop the administration by themselves by removing the patch from the application site if any adverse effect occurs.

Administration of the humoral immunity induction-promoting composition of the present invention or the vaccine pharmaceutical composition of the present invention provides a significantly improved antibody production inducing effect as compared to administration of an antigen alone.

DESCRIPTION OF EMBODIMENTS

The present invention will be specifically described in further detail below. The present invention, however, is not limited to these examples.

EXAMPLES 1 to 14, Comparative Examples 1 and 2

(Preparation of Solution for Transmucosal Administration)

A solution for transmucosal administration (transnasal administration or sublingual administration) was prepared according to the formulation shown in Tables 1 and 2 below. Specifically, an antigen (ovalbumin (OVA)) and a humoral immunity induction promoter whose active ingredient was a thrombosis treatment drug were blended in the amounts shown in Tables 1 and 2. For transnasal administration, saline was added thereto suth that the amount of the resulting mixture was 10 μL. For sublingual administration, saline was added such that the amount of the resulting mixture was 30 μL. This was followed by mixing to provide a solution for transmucosal administration (transnasal administration or sublingual administration).

As the humoral immunity induction promoter whose active ingredient is a thrombosis treatment drug, rivaroxaban (ChemScene, LLC), apixaban (ChemScene, LLC), argatroban (LKT Laboratories), nafamostat mesylate (Wako Pure Chemical Industries, Ltd.), camostat mesylate (Wako Pure Chemical Industries, Ltd.), gabexate mesylate (Wako Pure Chemical Industries, Ltd.), and tirofiban (Sigma-Aldrich) were used.

EXAMPLES 15 to 28, Comparative Examples 3 and 4

(Preparation of Solid Formulation for Sublingual Administration)

A solid formulation (freeze-dry formulation or film) for sublingual administration was prepared according to the formulation shown in Table 3 below. Specifically, an antigen (ovalbumin (OVA)), a humoral immunity induction promoter whose active ingredient was a thrombosis treatment drug, and hydroxypropylcellulose (HPC-SSL, Nippon Soda Co., Ltd.) as abase were blended in the amounts shown in Table 3. Saline was added thereto, followed by mixing to provide a formulation solution. Thereafter, 25 mg of the formulation solution was dispensed, and the dispensed solution was freeze-dried to provide a freeze-dry formulation or dried under reduced pressure to provide a film. The humoral immunity induction promoter whose active ingredient was a thrombosis treatment drug was the same as that used for preparing the solution for transmucosal administration.

<Evaluation 1>

Each of the solutions for transmucosal administration and solid formulations for sublingual administration obtained in the examples and the comparative examples was subjected to the following evaluation.

(Evaluation of Humoral Immunity Inducing Effect)

Figure 1:
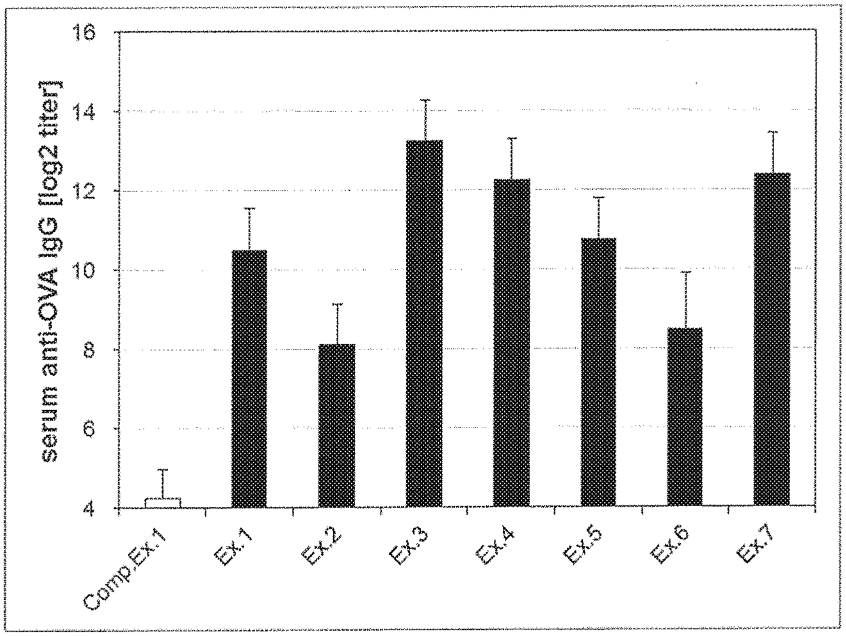
FIG. 1 shows an antigen (OVA)-specific IgG antibody titer in mouse serum after transnasal administration of solutions for transmucosal administration obtained in Examples 1 to 7 and Comparative Example 1.
Figure 2:
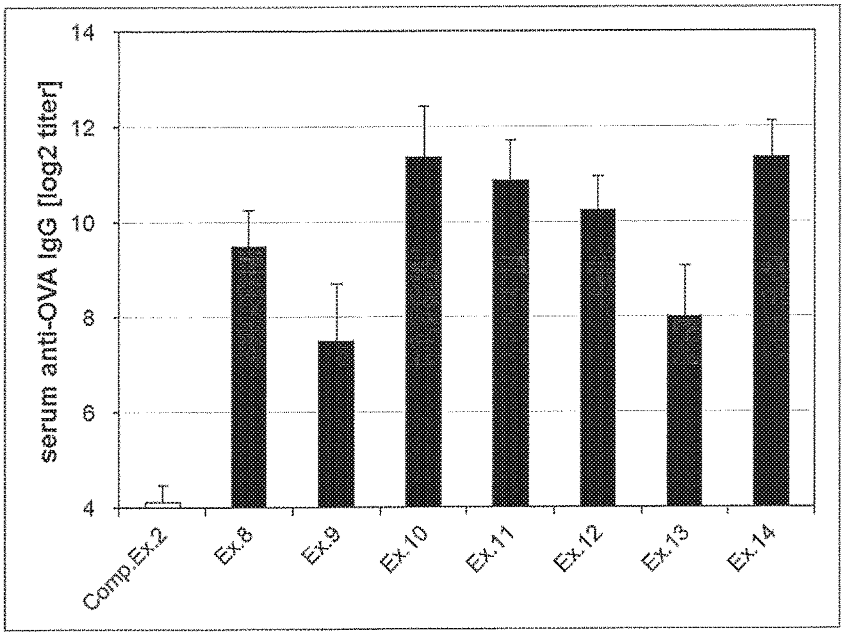
FIG. 2 shows an antigen (OVA)-specific IgG antibody titer in mouse serum after sublingual administration of solutions for transmucosal administration obtained in Examples 8 to 14 and Comparative Example 2.
Figure 3:
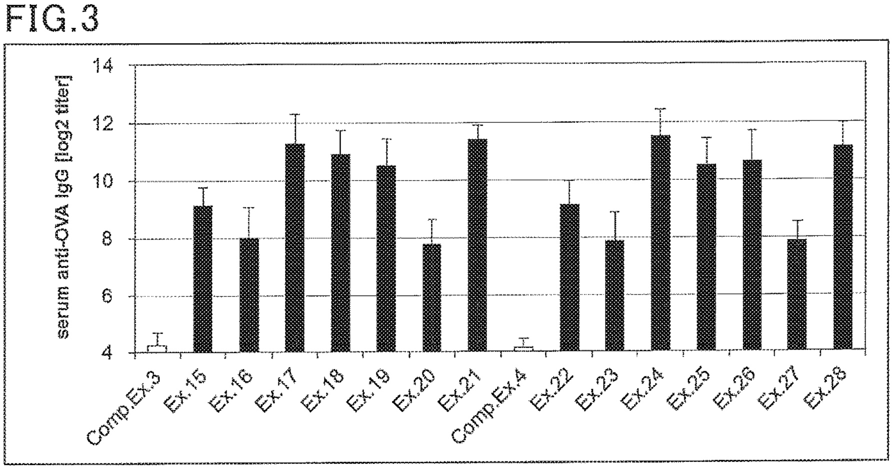
FIG. 3 shows an antigen (OVA)-specific IgG antibody titer in mouse serum after sublingual administration of solid formulations for sublingual administration obtained in Examples 15 to 28 and Comparative Examples 3 and 4.

A mouse immunity test using an animal model for immunological evaluation was performed with the solution for transmucosal administration or the solid formulation for sublingual administration by the following procedure. Thereafter, the systemic immune response was evaluated by determining the antigen (OVA)-specific IgG antibody titer in mouse serum. The results are shown in FIG. 1, 2, or 3.

(1) Mouse Immunity Test of Solution for Transmucosal Administration or Solid Formulation for Sublingual Administration A mouse (BALB/c mouse, female, 7 weeks old) was provided in advance. After the mouse was anesthetized, the solution for transmucosal administration was administered to the mouse by transnasal administration (10 μL, Examples 1 to 7 and Comparative Example 1 (Table 1)) or sublingual administration (30 μL, Examples to 14 and Comparative Example 2 (Table 2)). Similarly, the solid formulation for sublingual administration (Examples 15 to 28 and Comparative Examples 3 and 4 (Table 3)) was administered. One week after the administration, the mouse was anesthetized again, and the administration was performed again in the same manner. One week after the second administration, the mouse serum was taken.

(2) ELISA (Method for Determining Antigen-Specific IgG Antibody Titer in Mouse Serum (ELISA))

To each well of a 96-well plate for ELISA was added 100 μL of an OVA-containing solution (100 μg/mL) diluted with carbonate buffer, followed by standing overnight.

The wells were washed three times with preliminarily prepared wash (Tween 20-containing PBS), and to each well was added 200 μL of a blocking solution prepared by diluting a blocking agent (Block Ace, Sumitomo Dainippon Pharma Co., Ltd.) in purified water to 4 g/100 mL. This was followed by standing for 2 hours at room temperature. The wells were then washed three times with wash.

The serum taken from the mouse was centrifuged at 4° C. and 3,000 g for 10 minutes, and the supernatant was recovered. The supernatant was diluted in two-fold increments using a solution prepared by diluting a blocking agent in a phosphate buffer (Nacalai Tesque, Inc.) to 0.4 g/100 mL. The diluted solution was added to wells (50 μL for each well), followed by standing for hours at room temperature.

The wells were then washed three times with wash. An HRP-labeled anti-mouse IgG antibody (Goat-anti mouse IgG Fc HRP, BETHYL) was diluted 10,000-fold using a solution prepared by diluting a blocking agent in a phosphate buffer (Nacalai Tesque, Inc.) to 0.4 g/100 mL. To each well was added 100 μL of the resulting solution, followed by standing for 1 hour at room temperature.

The wells were then washed three times with wash, and 100 μL of a TMB solution (ELISA POD TMB kit, Nacalai Tesque, Inc.) was added to each well, followed by standing for 30 minutes at dark place.

Thereafter, 100 μL of a 1M sulfuric acid solution was added to each well, and the 96-well plate was subjected to measurement of absorbance at 450 nm with a microplate reader (Spectra Max M2$^e$, molecular device). The IgG antibody titer in the mouse serum was determined as Log 2 titer based on the absorbance at the incremental dilution.

TABLE 1

| | | | Antigen | | Immunity induction promoter | | Immunological | IgG antibody |
|---|---|---|---|---|---|---|---|---|
| No. | Administration route | Dosage form | Name | Amount [ug] | Name | Amount [ug] | evaluation mouse | titer [Log2 titer] |
| Comp. Ex. 1 | Transnasal | Solution | OVA | 1 | — | — | BALB/c | 4.3 |
| Ex. 1 | Transnasal | Solution | OVA | 1 | Rivaroxaban | 20 | BALB/c | 10.5 |
| Ex. 2 | Transnasal | Solution | OVA | 1 | Apixaban | 50 | BALB/c | 8.1 |

TABLE 1-continued

| No. | Administration route | Dosage form | Antigen Name | Antigen Amount [ug] | Immunity induction promoter Name | Immunity induction promoter Amount [ug] | Immunological evaluation mouse | IgG antibody titer [Log2 titer] |
|---|---|---|---|---|---|---|---|---|
| Ex. 3 | Transnasal | Solution | OVA | 1 | Argatroban | 20 | BALB/c | 13.3 |
| Ex. 4 | Transnasal | Solution | OVA | 1 | Nafamostat mesylate | 20 | BALB/c | 12.3 |
| Ex. 5 | Transnasal | Solution | OVA | 1 | Camostat mesylate | 20 | BALB/c | 10.8 |
| Ex. 6 | Transnasal | Solution | OVA | 1 | Gabexate mesylate | 20 | BALB/c | 8.5 |
| Ex. 7 | Transnasal | Solution | OVA | 1 | Tirofiban | 20 | BALB/c | 12.4 |

TABLE 2

| No. | Administration route | Dosage form | Antigen Name | Antigen Amount [ug] | Immunity induction promoter Name | Immunity induction promoter Amount [ug] | Immunological evaluation mouse | IgG antibody titer [Log2 titer] |
|---|---|---|---|---|---|---|---|---|
| Comp. Ex. 2 | Sublingual | Solution | OVA | 1 | — | — | BALB/c | 4.1 |
| Ex. 8 | Sublingual | Solution | OVA | 1 | Rivaroxaban | 100 | BALB/c | 9.5 |
| Ex. 9 | Sublingual | Solution | OVA | 1 | Apixaban | 100 | BALB/c | 7.5 |
| Ex. 10 | Sublingual | Solution | OVA | 1 | Argatroban | 100 | BALB/c | 11.4 |
| Ex. 11 | Sublingual | Solution | OVA | 1 | Nafamostat mesylate | 50 | BALB/c | 10.9 |
| Ex. 12 | Sublingual | Solution | OVA | 1 | Camostat mesylate | 100 | BALB/c | 10.3 |
| Ex. 13 | Sublingual | Solution | OVA | 1 | Gabexate mesylate | 100 | BALB/c | 8.0 |
| Ex. 14 | Sublingual | Solution | OVA | 1 | Tirofiban | 100 | BALB/c | 11.4 |

TABLE 3

| | | | Formulation [Parts by weight] | | | | | | | | | | | | | | | |
|---|---|---|---|---|---|---|---|---|---|---|---|---|---|---|---|---|---|---|
| | | | Ex. | | | | | | | | | | | | | | Comp. Ex. | |
| Component | | | 15 | 16 | 17 | 18 | 19 | 20 | 21 | 22 | 23 | 24 | 25 | 26 | 27 | 28 | 3 | 4 |
| Antigen | | OVA | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Immunity induction promoter | Name | Rivaroxaban | 10 | — | — | — | — | — | — | 10 | — | — | — | — | — | — | — | — |
| | | Apixaban | — | 10 | — | — | — | — | — | — | 10 | — | — | — | — | — | | |
| | | Argatroban | — | — | 10 | — | — | — | — | — | — | 10 | — | — | — | — | | |
| | | Nafamostat mesylate | — | — | — | 5 | — | — | — | — | — | — | 5 | — | — | — | — | — |
| | | Camostat mesylate | — | — | — | — | 10 | — | — | — | — | — | — | 10 | — | — | — | — |
| | | Gabexate mesylate | — | — | — | — | — | 10 | — | — | — | — | — | — | 10 | — | — | — |
| | | Tirofiban | — | — | — | — | — | — | 10 | — | — | — | — | — | — | 10 | — | — |
| Base | | HPC-SSL | 250 | 250 | 250 | 250 | 250 | 250 | 250 | 250 | 250 | 250 | 250 | 250 | 250 | 250 | 250 | 250 |
| Saline | | | 739.9 | 739.9 | 739.9 | 744.9 | 739.9 | 739.9 | 739.9 | 739.9 | 739.9 | 739.9 | 744.9 | 739.9 | 739.9 | 739.9 | 749.9 | 749.9 |
| Dispensing amount [mg/mouse] | | | 25 | 25 | 25 | 25 | 25 | 25 | 25 | 25 | 25 | 25 | 25 | 25 | 25 | 25 | 25 | 25 |
| IgG antibody titer [Log2 titer] | | | 9.1 | 8.0 | 11.3 | 10.9 | 10.5 | 7.8 | 11.4 | 9.1 | 7.9 | 11.5 | 10.5 | 10.6 | 7.9 | 11.1 | 4.3 | 4.1 |
| Dosage form | | | Solid (freeze dry) | | | | | | | Film | | | | | | | Solid (freeze dry) | Film |
| Administration route | | | Sublingual administration | | | | | | | | | | | | | | | |

EXAMPLES 29 to 33, Comparative Example 5

(Preparation of Solution for Subcutaneous Administration)

A formulation for subcutaneous administration was prepared according to the formulation shown in Table 4 below.

Specifically, an antigen (ovalbumin (OVA)) and a humoral immunity induction promoter whose active ingredient was a thrombosis treatment drug were blended in the amounts shown in Table 4. Saline was added thereto such that the amount of the resulting mixture was 200 μL, followed by mixing to provide a solution for subcutaneous administration.

<Evaluation 2>

Each of the formulations for subcutaneous administration obtained in the examples and the comparative examples was subjected to the following evaluation.

(Evaluation of Humoral Immunity Inducing Effect)

Figure 4:
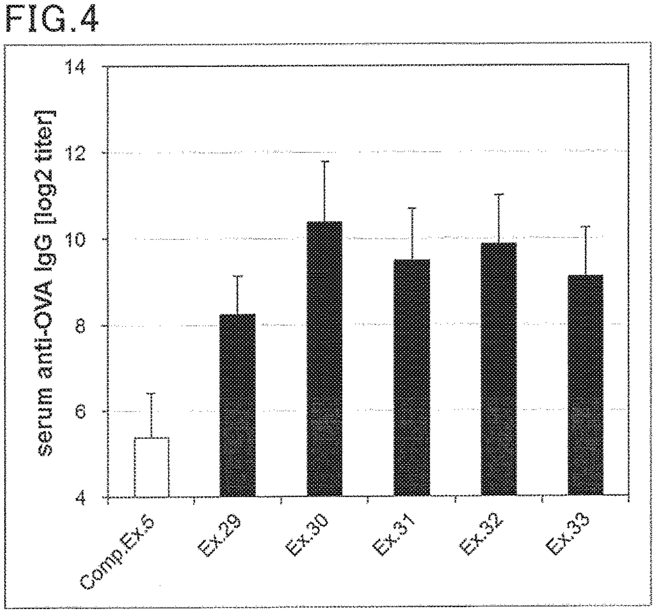
FIG. 4 shows an antigen (OVA)-specific IgG antibody titer in mouse serum after subcutaneous administration of solutions for subcutaneous administration obtained in Examples 29 to 33 and Comparative Example 5.

A mouse immunity test using an animal model for immunological evaluation was performed with the formulation for subcutaneous administration by the following procedure. Thereafter, the systemic immune response was evaluated by determining the antigen (OVA)-specific IgG antibody in mouse serum. The results are shown in FIG. 4.

(1) Mouse Immunity Test of Formulation for Subcutaneous Administration

A mouse (BALB/c mouse, female, 7 weeks old) was provided in advance. After the mouse was anesthetized, 200

μL of the formulation was subcutaneously administered to the skin of the back of the mouse. One week after the administration, the mouse was anesthetized again, and administration was performed again in the same manner. One week after the second administration, the mouse serum was taken.

(2) ELISA

The antigen (OVA)-specific IgG antibody titer in the mouse serum was determined by ELISA by the same procedure as in <Evaluation 1>.

PET-film side faced the tape. The cream in an amount of 4 mg was applied to the nonwoven fabric portion of the composite base to provide a sample for a mouse immunity test.

<Evaluation 3>

Each of the creams for transdermal administration obtained in the examples and the comparative examples was subjected to the following evaluation.

(Evaluation of Humoral Immunity Inducing Effect)

Figure 5:
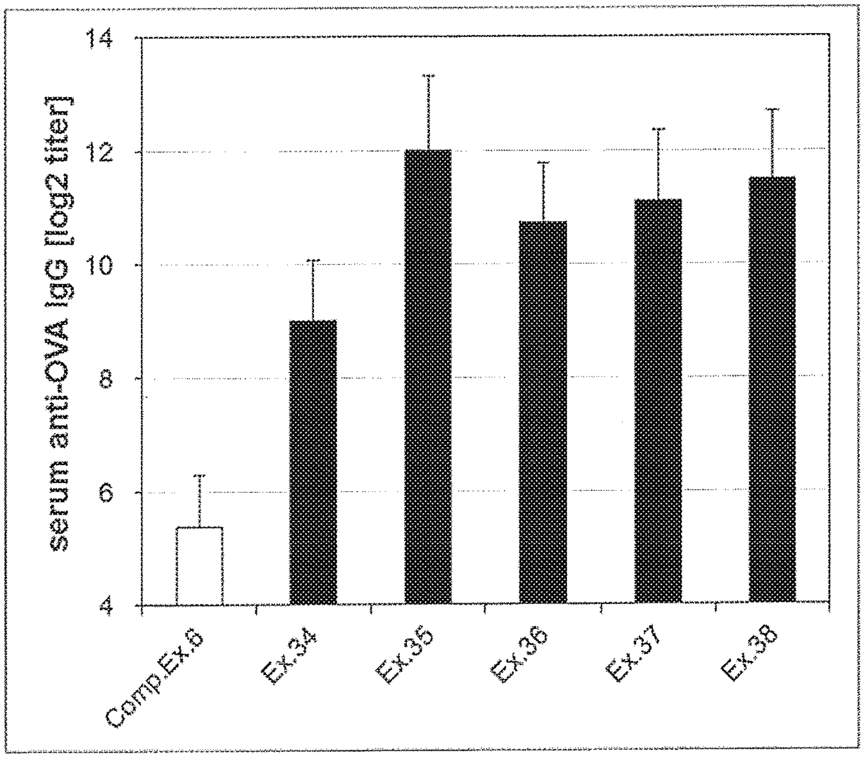
FIG. 5 shows an antigen (OVA)-specific IgG antibody titer in mouse serum after transdermal administration of creams for transdermal administration obtained in Examples 34 to 38 and Comparative Example 6.

A mouse immunity test using an animal model for immunological evaluation was performed with the cream for transdermal administration by the following procedure. Thereafter, the systemic immune response was evaluated by determining the antigen (OVA)-specific IgG antibody in mouse serum. The results are shown in FIG. 5.

TABLE 4

| | | | Antigen | | Immunity induction promoter | | Immunological | IgG antibody |
|---|---|---|---|---|---|---|---|---|
| No. | Administration route | Dosage form | Name | Amount [ug] | Name | Amount [ug] | evaluation mouse | titer [Log2 titer] |
| Comp. Ex. 5 | Subcutaneous | Solution | OVA | 0.05 | — | — | BALB/c | 5.4 |
| Ex. 29 | Subcutaneous | Solution | OVA | 0.05 | Rivaroxaban | 200 | BALB/c | 8.3 |
| Ex. 30 | Subcutaneous | Solution | OVA | 0.05 | Argatroban | 200 | BALB/c | 10.4 |
| Ex. 31 | Subcutaneous | Solution | OVA | 0.05 | Nafamostat mesylate | 200 | BALB/c | 9.5 |
| Ex. 32 | Subcutaneous | Solution | OVA | 0.05 | Camostat mesylate | 200 | BALB/c | 9.9 |
| Ex. 33 | Subcutaneous | Solution | OVA | 0.05 | Tirofiban | 200 | BALB/c | 9.1 |

EXAMPLES 34 to 38, Comparative Example 6

(Preparation of Cream for Transdermal Administration)

A cream for transdermal administration was prepared according to the formulation shown in Table 5 below. Specifically, an antigen (ovalbumin (OVA)) and a humoral immunity induction promoter whose active ingredient was a thrombosis treatment drug were blended in the amounts shown in Table 5 and a base (base cream) was added thereto to achieve a total weight of 100 parts by weight, followed by mixing to provide a cream for transdermal administration. The base cream was prepared by blending and mixing materials according to the formulation shown in Table 6.

The humoral immunity induction promoter whose active ingredient was a thrombosis treatment drug was the same as that used for preparing the solutions for transnasal or sublingual administration. White Vaseline, sorbitan monostearate, isostearic acid, benzyl alcohol, stearyl alcohol, polysorbate 60, and concentrated glycerin were purchased from Wako Pure Chemical Industries, Ltd. Cetanol was purchased from Tokyo Chemical Industry Co., Ltd.

A composite base was prepared by bonding a PET film/PET nonwoven fabric laminate (area: 0.7 $cm^2$) to the center portion of an adhesive tape for attachment such that the (1) Mouse Immunity Test of Cream for Transdermal Administration The right back of a mouse (C57BL6 NCr mouse, female, 7 weeks old) was shaved in advance. After a rearing period for recovery from the skin damage caused by the shaving, 4 mg of the cream for transdermal administration was administered to the skin of the right back of the mouse, and the left back was shaved at the same time. Twenty-four hours later, the cream for transdermal administration on the right back was removed. One week after the administration, the cream for transdermal administration was administered to the skin of the left back of the mouse in the same manner and removed 24 hours later. One week after the second administration, the mouse serum was taken.

(2) ELISA

The antigen (OVA)-specific IgG antibody titer in the mouse serum was determined by ELISA by the same procedure as in <Evaluation 1>.

TABLE 5

| | | | Antigen | | Immunity induction promoter | | | |
|---|---|---|---|---|---|---|---|---|
| No. | Administration route | Dosage form | Name | Amount [Parts by weight] | Name | Amount [Parts by weight] | Immunological evaluation mouse | IgG antibody titer [Log2 titer] |
| Comp. Ex. 6 | Transdermal | Cream | OVA | 5 | — | — | C57BL6 | 5.4 |
| Ex. 34 | Transdermal | Cream | OVA | 5 | Rivaroxaban | 5 | C57BL6 | 9.0 |
| Ex. 35 | Transdermal | Cream | OVA | 5 | Argatroban | 5 | C57BL6 | 12.0 |
| Ex. 36 | Transdermal | Cream | OVA | 5 | Nafamostat mesylate | 5 | C57BL6 | 10.8 |
| Ex. 37 | Transdermal | Cream | OVA | 5 | Camostat mesylate | 5 | C57BL6 | 11.1 |
| Ex. 38 | Transdermal | Cream | OVA | 5 | Tirofiban | 5 | C57BL6 | 11.5 |

TABLE 6

| Additve | Amount [Parts by weight] |
|---|---|
| White Vaseline | 60.7 |
| Sorbitan monostearate | 0.7 |
| Isostearic acid | 12 |
| Benzyl alcohol | 2.4 |
| Cetanol | 2.4 |
| Stearyl alcohol | 3.5 |
| Polysorbate 60 | 3.5 |
| Concentrated glycerin | 2.4 |
| Purified water | 12.4 |
| Total | 100 |

EXAMPLES 39 to 198, Comparative Examples 7 to 46

A solution for transmucosal administration (transnasal administration or sublingual administration) was prepared according to the formulation shown in Tables 7 to 11 below. Specifically, an antigen and a humoral immunity induction promoter whose active ingredient was a thrombosis treatment drug were blended in the amounts shown in Tables 7 to 11. For transnasal administration, saline was added thereto so that the amount of the resulting mixture was 10 μL. For sublingual administration, saline was added so that the amount of the resulting mixture was 30 μL. This was followed by mixing to provide a solution for transmucosal administration (transnasal administration or sublingual administration).

Influenza vaccine antigens used were an influenza vaccine antigen-containing solution H1N1 (A/California/07/2009, The Research Foundation for Microbial Diseases of Osaka University), H3N2 (A/Victoria361/2011, The Research Foundation for Microbial Diseases of Osaka University), Influenza B virus (B/Wisconsin/1/2010, The Research Foundation for Microbial Diseases of Osaka University), Influenza B virus (B/Brisbane/60/2008, The Research Foundation for Microbial Diseases of Osaka University) were used. Also used were a pneumococcal capsular polysaccharide-containing solution (Pneumovax NP, MSD), HPV16 recombinant protein-containing solution (HPV16, PROSPEC), a live attenuated rotavirus-containing solution (RotaTeq Oral Solution, MSD), an inactivated poliovirus-containing solution (IMOVAX POLIO for subcutaneous injection, Sanofi), an inactivated hepatitis A virus-containing solution (Aimmugen, The Chemo-Sero-Therapeutic Research Institute), an inactivated Japanese encephalitis virus-containing solution (Encevac for subcutaneous injection, The Chemo-Sero-Therapeutic Research Institute), a live attenuated mumps virus-containing solution (live mumps vaccine, Kitasato Daiichi Sankyo Vaccine Co., Ltd), a live attenuated measles virus-containing solution (live measles vaccine, Kitasato Daiichi Sankyo Vaccine Co., Ltd), a live attenuated rubella virus-containing solution (dried live attenuated rubella vaccine, Kitasato Daiichi Sankyo Vaccine Co., Ltd), a solution containing tetanus toxoid-conjugated haemophilus influenzae type b polysaccharide (ActHIB, Sanofi), a recombinant HBs antigen protein-containing solution (Bimmugen, The Chemo-Sero-Therapeutic Research Institute), a live attenuated yellow fever virus-containing solution (yellow fever vaccine, Sanofi), a tetanus toxoid-containing solution (tetanus toxoid, Denka Seiken Co., Ltd.), a live attenuated varicella virus-containing solution (dried live attenuated varicella vaccine, The Research Foundation for Microbial Diseases of Osaka University), a live BCG-containing solution (dried BCG vaccine, Japan BCG Laboratory), and an inactivated rabies virus-containing solution (tissue-cultured inactivated rabies vaccine, The Chemo-Sero-Therapeutic Research Institute).

As the humoral immunity induction promoter whose active ingredient was a thrombosis treatment drug, argatroban (LKT Laboratories), nafamostat mesylate (Wako Pure Chemical Industries, Ltd.), camostat mesylate (Wako Pure Chemical Industries, Ltd.), and tirofiban (Sigma-Aldrich) were used.

<Evaluation 4>

Each of the solutions for transmucosal administration obtained in the examples and the comparative examples was subjected to the following evaluation.

(Evaluation of Humoral Immunity Inducing Effect)

A mouse immunity test using an animal model for immunological evaluation was performed with the solution for transmucosal administration by the following procedure. Thereafter, the systemic immune response was evaluated by determining the antigen (OVA)-specific IgG antibody in mouse serum.

(1) Mouse Immunity Test of Solution for Transmucosal Administration

Mouse serum was taken by the same procedure as in <Evaluation 1>, an evaluation of solution for transmucosal administration or sublingual administration.

(2) ELISA

The antigen (OVA)-specific IgG antibody titer in the mouse serum was determined by ELISA by the same procedure as in <Evaluation 1>, an evaluation of solution for transmucosal administration or sublingual administration.

The evaluation of the humoral immunity inducing effect shows that the transmucosal administration (transnasal administration or sublingual administration) of a solution for transmucosal administration containing a humoral immunity induction promoter whose active ingredient is a thrombosis treatment drug (Examples 1 to 14) provides a higher antigen-specific IgG antibody titer than the administration of a solution for transmucosal administration free from a humoral immunity induction promoter whose active ingredient is a thrombosis treatment drug (Comparative Examples 1 and 2).

Accordingly, also when antigens such as those shown in Tables 7 to 11 below are used, the use of a humoral immunity induction promoter whose active ingredient is a thrombosis treatment drug leads to a high antigen-specific IgG antibody titer.

TABLE 7

| | Antigen | | Immunity induction promoter | | | | |
|---|---|---|---|---|---|---|---|
| | Name | Amount [μg] | Name | Amount [μg] | Dosage form | Administration route | Amount [μL] |
| Comp. Ex. 7 | A/California/07/2009 [H1N1] | 1.0 | — | — | Solution | Transnasal | 10 |
| Ex. 39 | A/California/07/2009 [H1N1] | 1.0 | Argatroban | 20 | Solution | Transnasal | 10 |

TABLE 7-continued

| | Antigen | | Immunity induction promoter | | | | |
|---|---|---|---|---|---|---|---|
| | Name | Amount [μg] | Name | Amount [μg] | Dosage form | Administration route | Amount [μL] |
| Ex. 40 | A/California/07/2009 [H1N1] | 1.0 | Nafamostat mesylate | 20 | Solution | Transnasal | 10 |
| Ex. 41 | A/California/07/2009 [H1N1] | 1.0 | Camostat mesylate | 20 | Solution | Transnasal | 10 |
| Ex. 42 | A/California/07/2009 [H1N1] | 1.0 | Tirofiban | 20 | Solution | Transnasal | 10 |
| Ex. 43 | A/California/07/2009 [H1N1] | 1.0 | — | — | Solution | Sublingual | 30 |
| Comp. Ex. 8 | A/California/07/2009 [H1N1] | 1.0 | Argatroban | 100 | Solution | Sublingual | 30 |
| Ex. 44 | A/California/07/2009 [H1N1] | 1.0 | Nafamostat mesylate | 100 | Solution | Sublingual | 30 |
| Ex. 45 | A/California/07/2009 [H1N1] | 1.0 | Camostat mesylate | 100 | Solution | Sublingual | 30 |
| Ex. 46 | A/California/07/2009 [H1N1] | 1.0 | Tirofiban | 100 | Solution | Sublingual | 30 |
| Comp. Ex. 9 | A/Victoria361/2011 [H3N2] | 1.0 | — | — | Solution | Transnasal | 10 |
| Ex. 47 | A/Victoria361/2011 [H3N2] | 1.0 | Argatroban | 20 | Solution | Transnasal | 10 |
| Ex. 48 | A/Victoria361/2011 [H3N2] | 1.0 | Nafamostat mesylate | 20 | Solution | Transnasal | 10 |
| Ex. 49 | A/Victoria361/2011 [H3N2] | 1.0 | Camostat mesylate | 20 | Solution | Transnasal | 10 |
| Ex. 50 | A/Victoria361/2011 [H3N2] | 1.0 | Tirofiban | 20 | Solution | Transnasal | 10 |
| Comp. Ex. 10 | A/Victoria361/2011 [H3N2] | 1.0 | — | — | Solution | Sublingual | 30 |
| Ex. 51 | A/Victoria361/2011 [H3N2] | 1.0 | Argatroban | 100 | Solution | Sublingual | 30 |
| Ex. 52 | A/Victoria361/2011 [H3N2] | 1.0 | Nafamostat mesylate | 100 | Solution | Sublingual | 30 |
| Ex. 53 | A/Victoria361/2011 [H3N2] | 1.0 | Camostat mesylate | 100 | Solution | Sublingual | 30 |
| Ex. 54 | A/Victoria361/2011 [H3N2] | 1.0 | Tirofiban | 100 | Solution | Sublingual | 30 |
| Comp. Ex. 11 | B/Wisconsin/1/2010 | 1.0 | — | — | Solution | Transnasal | 10 |
| Ex. 55 | B/Wisconsin/1/2010 | 1.0 | Argatroban | 20 | Solution | Transnasal | 10 |
| Ex. 56 | B/Wisconsin/1/2010 | 1.0 | Nafamostat mesylate | 20 | Solution | Transnasal | 10 |
| Ex. 57 | B/Wisconsin/1/2010 | 1.0 | Camostat mesylate | 20 | Solution | Transnasal | 10 |
| Ex. 58 | B/Wisconsin/1/2010 | 1.0 | Tirofiban | 20 | Solution | Transnasal | 10 |
| Comp. Ex. 12 | B/Wisconsin/1/2010 | 1.0 | — | — | Solution | Sublingual | 30 |
| Ex. 59 | B/Wisconsin/1/2010 | 1.0 | Argatroban | 100 | Solution | Sublingual | 30 |
| Ex. 60 | B/Wisconsin/1/2010 | 1.0 | Nafamostat mesylate | 100 | Solution | Sublingual | 30 |
| Ex. 61 | B/Wisconsin/1/2010 | 1.0 | Camostat mesylate | 100 | Solution | Sublingual | 30 |
| Ex. 62 | B/Wisconsin/1/2010 | 1.0 | Tirofiban | 100 | Solution | Sublingual | 30 |
| Comp. Ex. 13 | B/Brisbane/60/2008 | 1.0 | — | — | Solution | Transnasal | 10 |
| Ex. 63 | B/Brisbane/60/2008 | 1.0 | Argatroban | 20 | Solution | Transnasal | 10 |
| Ex. 64 | B/Brisbane/60/2008 | 1.0 | Nafamostat mesylate | 20 | Solution | Transnasal | 10 |
| Ex. 65 | B/Brisbane/60/2008 | 1.0 | Camostat mesylate | 20 | Solution | Transnasal | 10 |
| Ex. 66 | B/Brisbane/60/2008 | 1.0 | Tirofiban | 20 | Solution | Transnasal | 10 |
| Comp. Ex. 14 | B/Brisbane/60/2008 | 1.0 | — | — | Solution | Sublingual | 30 |
| Ex. 67 | B/Brisbane/60/2008 | 1.0 | Argatroban | 100 | Solution | Sublingual | 30 |
| Ex. 68 | B/Brisbane/60/2008 | 1.0 | Nafamostat mesylate | 100 | Solution | Sublingual | 30 |
| Ex. 69 | B/Brisbane/60/2008 | 1.0 | Camostat mesylate | 100 | Solution | Sublingual | 30 |
| Ex. 70 | B/Brisbane/60/2008 | 1.0 | Tirofiban | 100 | Solution | Sublingual | 30 |

TABLE 8

| | Antigen | | Immunity induction promoter | | | | |
|---|---|---|---|---|---|---|---|
| | Name | Amount [μg] | Name | Amount [μg] | Dosage form | Administration route | Amount [μL] |
| Comp. Ex. 15 | Pneumococcal capsular polysaccharide Pneumovax NP | 20 | — | — | Solution | Transnasal | 10 |
| Ex. 71 | Pneumococcal capsular polysaccharide Pneumovax NP | 20 | Argatroban | 20 | Solution | Transnasal | 10 |
| Ex. 72 | Pneumococcal capsular polysaccharide Pneumovax NP | 20 | Nafamostat mesylate | 20 | Solution | Transnasal | 10 |
| Ex. 73 | Pneumococcal capsular polysaccharide Pneumovax NP | 20 | Camostat mesylate | 20 | Solution | Transnasal | 10 |
| Ex. 74 | Pneumococcal capsular polysaccharide Pneumovax NP | 20 | Tirofiban | 20 | Solution | Transnasal | 10 |
| Comp. Ex. 16 | Pneumococcal capsular polysaccharide Pneumovax NP | 20 | — | — | Solution | Sublingual | 30 |
| Ex. 75 | Pneumococcal capsular polysaccharide Pneumovax NP | 20 | Argatroban | 100 | Solution | Sublingual | 30 |
| Ex. 76 | Pneumococcal capsular polysaccharide Pneumovax NP | 20 | Nafamostat mesylate | 100 | Solution | Sublingual | 30 |
| Ex. 77 | Pneumococcal capsular polysaccharide Pneumovax NP | 20 | Camostat mesylate | 100 | Solution | Sublingual | 30 |

TABLE 8-continued

| | Antigen | | Immunity induction promoter | | | | |
|---|---|---|---|---|---|---|---|
| | Name | Amount [μg] | Name | Amount [μg] | Dosage form | Administration route | Amount [μL] |
| Ex. 78 | Pneumococcal capsular polysaccharide Pneumovax NP | 20 | Tirofiban | 100 | Solution | Sublingual | 30 |
| Comp. Ex. 17 | HPV16 recombinant protein | 10 | — | — | Solution | Transnasal | 10 |
| Ex. 79 | HPV16 recombinant protein | 10 | Argatroban | 20 | Solution | Transnasal | 10 |
| Ex. 80 | HPV16 recombinant protein | 10 | Nafamostat mesylate | 20 | Solution | Transnasal | 10 |
| Ex. 81 | HPV16 recombinant protein | 10 | Camostat mesylate | 20 | Solution | Transnasal | 10 |
| Ex. 82 | HPV16 recombinant protein | 10 | Tirofiban | 20 | Solution | Transnasal | 10 |
| Comp. Ex. 18 | HPV16 recombinant protein | 10 | — | — | Solution | Sublingual | 30 |
| Ex. 83 | HPV16 recombinant protein | 10 | Argatroban | 100 | Solution | Sublingual | 30 |
| Ex. 84 | HPV16 recombinant protein | 10 | Nafamostat mesylate | 100 | Solution | Sublingual | 30 |
| Ex. 85 | HPV16 recombinant protein | 10 | Camostat mesylate | 100 | Solution | Sublingual | 30 |
| Ex. 86 | HPV16 recombinant protein | 10 | Tirofiban | 100 | Solution | Sublingual | 30 |
| Comp. Ex. 19 | Live attenuated rotavirus (RIX4414 strain) | 10 | — | — | Solution | Transnasal | 10 |
| Ex. 87 | Live attenuated rotavirus (RIX4414 strain) | 10 | Argatroban | 20 | Solution | Transnasal | 10 |
| Ex. 88 | Live attenuated rotavirus (RIX4414 strain) | 10 | Nafamostat mesylate | 20 | Solution | Transnasal | 10 |
| Ex. 89 | Live attenuated rotavirus (RIX4414 strain) | 10 | Camostat mesylate | 20 | Solution | Transnasal | 10 |
| Ex. 90 | Live attenuated rotavirus (RIX4414 strain) | 10 | Tirofiban | 20 | Solution | Transnasal | 10 |
| Comp. Ex. 20 | Live attenuated rotavirus (RIX4414 strain) | 10 | — | — | Solution | Sublingual | 30 |
| Ex. 91 | Live attenuated rotavirus (RIX4414 strain) | 10 | Argatroban | 100 | Solution | Sublingual | 30 |
| Ex. 92 | Live attenuated rotavirus (RIX4414 strain) | 10 | Nafamostat mesylate | 100 | Solution | Sublingual | 30 |
| Ex. 93 | Live attenuated rotavirus (RIX4414 strain) | 10 | Camostat mesylate | 100 | Solution | Sublingual | 30 |
| Ex. 94 | Live attenuated rotavirus (RIX4414 strain) | 10 | Tirofiban | 100 | Solution | Sublingual | 30 |
| Comp. Ex. 21 | Inactivated poliovirus (type 1, type 2, and type 3) | Vaccine 100 μL equivalent | — | — | Solution | Transnasal | 10 |
| Ex. 95 | Inactivated poliovirus (type 1, type 2, and type 3) | Vaccine 100 μL equivalent | Argatroban | 20 | Solution | Transnasal | 10 |
| Ex. 96 | Inactivated poliovirus (type 1, type 2, and type 3) | Vaccine 100 μL equivalent | Nafamostat mesylate | 20 | Solution | Transnasal | 10 |
| Ex. 97 | Inactivated poliovirus (type 1, type 2, and type 3) | Vaccine 100 μL equivalent | Camostat mesylate | 20 | Solution | Transnasal | 10 |
| Ex. 98 | Inactivated poliovirus (type 1, type 2, and type 3) | Vaccine 100 μL equivalent | Tirofiban | 20 | Solution | Transnasal | 10 |
| Comp. Ex. 22 | Inactivated poliovirus (type 1, type 2, and type 3) | Vaccine 100 μL equivalent | — | — | Solution | Sublingual | 30 |
| Ex. 99 | Inactivated poliovirus (type 1, type 2, and type 3) | Vaccine 100 μL equivalent | Argatroban | 100 | Solution | Sublingual | 30 |
| Ex. 100 | Inactivated poliovirus (type 1, type 2, and type 3) | Vaccine 100 μL equivalent | Nafamostat mesylate | 100 | Solution | Sublingual | 30 |
| Ex. 101 | Inactivated poliovirus (type 1, type 2, and type 3) | Vaccine 100 μL equivalent | Camostat mesylate | 100 | Solution | Sublingual | 30 |
| Ex. 102 | Inactivated poliovirus (type 1, type 2, and type 3) | Vaccine 100 μL equivalent | Tirofiban | 100 | Solution | Sublingual | 30 |

TABLE 9

| | Antigen | | Immunity induction promoter | | | | |
|---|---|---|---|---|---|---|---|
| | Name | Amount [μg] | Name | Amount [μg] | Dosage form | Administration route | Amount [μL] |
| Comp. Ex. 23 | Inactivated hepatitis A virus | Vaccine 100 μL equivalent | — | — | Solution | Transnasal | 10 |
| Ex. 103 | Inactivated hepatitis A virus | Vaccine 100 μL equivalent | Argatroban | 20 | Solution | Transnasal | 10 |
| Ex. 104 | Inactivated hepatitis A virus | Vaccine 100 μL equivalent | Nafamostat mesylate | 20 | Solution | Transnasal | 10 |
| Ex. 105 | Inactivated hepatitis A virus | Vaccine 100 μL equivalent | Camostat mesylate | 20 | Solution | Transnasal | 10 |
| Ex. 106 | Inactivated hepatitis A virus | Vaccine 100 μL equivalent | Tirofiban | 20 | Solution | Transnasal | 10 |

TABLE 9-continued

| | Antigen | | Immunity induction promoter | | | | |
|---|---|---|---|---|---|---|---|
| | Name | Amount [μg] | Name | Amount [μg] | Dosage form | Administration route | Amount [μL] |
| Comp. Ex. 24 | Inactivated hepatitis A virus | Vaccine 100 μL equivalent | — | — | Solution | Sublingual | 30 |
| Ex. 107 | Inactivated hepatitis A virus | Vaccine 100 μL equivalent | Argatroban | 100 | Solution | Sublingual | 30 |
| Ex. 108 | Inactivated hepatitis A virus | Vaccine 100 μL equivalent | Nafamostat mesylate | 100 | Solution | Sublingual | 30 |
| Ex. 109 | Inactivated hepatitis A virus | Vaccine 100 μL equivalent | Camostat mesylate | 100 | Solution | Sublingual | 30 |
| Ex. 110 | Inactivated hepatitis A virus | Vaccine 100 μL equivalent | Tirofiban | 100 | Solution | Sublingual | 30 |
| Comp. Ex. 25 | Inactivated Japanese encephalitis virus | Vaccine 100 μL equivalent | — | — | Solution | Transnasal | 10 |
| Ex. 111 | Inactivated Japanese encephalitis virus | Vaccine 100 μL equivalent | Argatroban | 20 | Solution | Transnasal | 10 |
| Ex. 112 | Inactivated Japanese encephalitis virus | Vaccine 100 μL equivalent | Nafamostat mesylate | 20 | Solution | Transnasal | 10 |
| Ex. 113 | Inactivated Japanese encephalitis virus | Vaccine 100 μL equivalent | Camostat mesylate | 20 | Solution | Transnasal | 10 |
| Ex. 114 | Inactivated Japanese encephalitis virus | Vaccine 100 μL equivalent | Tirofiban | 20 | Solution | Transnasal | 10 |
| Comp. Ex. 26 | Inactivated Japanese encephalitis virus | Vaccine 100 μL equivalent | — | — | Solution | Sublingual | 30 |
| Ex. 115 | Inactivated Japanese encephalitis virus | Vaccine 100 μL equivalent | Argatroban | 100 | Solution | Sublingual | 30 |
| Ex. 116 | Inactivated Japanese encephalitis virus | Vaccine 100 μL equivalent | Nafamostat mesylate | 100 | Solution | Sublingual | 30 |
| Ex. 117 | Inactivated Japanese encephalitis virus | Vaccine 100 μL equivalent | Camostat mesylate | 100 | Solution | Sublingual | 30 |
| Ex. 118 | Inactivated Japanese encephalitis virus | Vaccine 100 μL equivalent | Tirofiban | 100 | Solution | Sublingual | 30 |
| Comp. Ex. 27 | Live attenuated mumps virus | Vaccine 100 μL equivalent | — | — | Solution | Transnasal | 10 |
| Ex. 119 | Live attenuated mumps virus | Vaccine 100 μL equivalent | Argatroban | 20 | Solution | Transnasal | 10 |
| Ex. 120 | Live attenuated mumps virus | Vaccine 100 μL equivalent | Nafamostat mesylate | 20 | Solution | Transnasal | 10 |
| Ex. 121 | Live attenuated mumps virus | Vaccine 100 μL equivalent | Camostat mesylate | 20 | Solution | Transnasal | 10 |
| Ex. 122 | Live attenuated mumps virus | Vaccine 100 μL equivalent | Tirofiban | 20 | Solution | Transnasal | 10 |
| Comp. Ex. 28 | Live attenuated mumps virus | Vaccine 100 μL equivalent | — | — | Solution | Sublingual | 30 |
| Ex. 123 | Live attenuated mumps virus | Vaccine 100 μL equivalent | Argatroban | 100 | Solution | Sublingual | 30 |
| Ex. 124 | Live attenuated mumps virus | Vaccine 100 μL equivalent | Nafamostat mesylate | 100 | Solution | Sublingual | 30 |
| Ex. 125 | Live attenuated mumps virus | Vaccine 100 μL equivalent | Camostat mesylate | 100 | Solution | Sublingual | 30 |
| Ex. 126 | Live attenuated mumps virus | Vaccine 100 μL equivalent | Tirofiban | 100 | Solution | Sublingual | 30 |
| Comp. Ex. 29 | Live attenuated measles virus | Vaccine 100 μL equivalent | — | — | Solution | Transnasal | 10 |
| Ex. 127 | Live attenuated measles virus | Vaccine 100 μL equivalent | Argatroban | 20 | Solution | Transnasal | 10 |
| Ex. 128 | Live attenuated measles virus | Vaccine 100 μL equivalent | Nafamostat mesylate | 20 | Solution | Transnasal | 10 |
| Ex. 129 | Live attenuated measles virus | Vaccine 100 μL equivalent | Camostat mesylate | 20 | Solution | Transnasal | 10 |
| Ex. 130 | Live attenuated measles virus | Vaccine 100 μL equivalent | Tirofiban | 20 | Solution | Transnasal | 10 |
| Comp. Ex. 30 | Live attenuated measles virus | Vaccine 100 μL equivalent | — | — | Solution | Sublingual | 30 |
| Ex. 131 | Live attenuated measles virus | Vaccine 100 μL equivalent | Argatroban | 100 | Solution | Sublingual | 30 |
| Ex. 132 | Live attenuated measles virus | Vaccine 100 μL equivalent | Nafamostat mesylate | 100 | Solution | Sublingual | 30 |
| Ex. 133 | Live attenuated measles virus | Vaccine 100 μL equivalent | Camostat mesylate | 100 | Solution | Sublingual | 30 |
| Ex. 134 | Live attenuated measles virus | Vaccine 100 μL equivalent | Tirofiban | 100 | Solution | Sublingual | 30 |

TABLE 10

| | Antigen | | Immunity induction promoter | | | | |
|---|---|---|---|---|---|---|---|
| | Name | Amount [μg] | Name | Amount [μg] | Dosage form | Administration route | Amount [μL] |
| Comp. Ex. 31 | Live attenuated rubella virus | Vaccine 100 μL equivalent | — | — | Solution | Transnasal | 10 |
| Ex. 135 | Live attenuated rubella virus | Vaccine 100 μL equivalent | Argatroban | 20 | Solution | Transnasal | 10 |
| Ex. 136 | Live attenuated rubella virus | Vaccine 100 μL equivalent | Nafamostat mesylate | 20 | Solution | Transnasal | 10 |
| Ex. 137 | Live attenuated rubella virus | Vaccine 100 μL equivalent | Camostat mesylate | 20 | Solution | Transnasal | 10 |
| Ex. 138 | Live attenuated rubella virus | Vaccine 100 μL equivalent | Tirofiban | 20 | Solution | Transnasal | 10 |
| Comp. Ex. 32 | Live attenuated rubella virus | Vaccine 100 μL equivalent | — | — | Solution | Sublingual | 30 |
| Ex. 139 | Live attenuated rubella virus | Vaccine 100 μL equivalent | Argatroban | 100 | Solution | Sublingual | 30 |
| Ex. 140 | Live attenuated rubella virus | Vaccine 100 μL equivalent | Nafamostat mesylate | 100 | Solution | Sublingual | 30 |
| Ex. 141 | Live attenuated rubella virus | Vaccine 100 μL equivalent | Camostat mesylate | 100 | Solution | Sublingual | 30 |
| Ex. 142 | Live attenuated rubella virus | Vaccine 100 μL equivalent | Tirofiban | 100 | Solution | Sublingual | 30 |
| Comp. Ex. 33 | Tetanus toxoid-conjugated Haemophilus influenzae type b polysaccharide | Vaccine 100 μL equivalent | — | — | Solution | Transnasal | 10 |
| Ex. 143 | Tetanus toxoid-conjugated Haemophilus influenzae type b polysaccharide | Vaccine 100 μL equivalent | Argatroban | 20 | Solution | Transnasal | 10 |
| Ex. 144 | Tetanus toxoid-conjugated Haemophilus influenzae type b polysaccharide | Vaccine 100 μL equivalent | Nafamostat mesylate | 20 | Solution | Transnasal | 10 |
| Ex. 145 | Tetanus toxoid-conjugated Haemophilus influenzae type b polysaccharide | Vaccine 100 μL equivalent | Camostat mesylate | 20 | Solution | Transnasal | 10 |
| Ex. 146 | Tetanus toxoid-conjugated Haemophilus influenzae type b polysaccharide | Vaccine 100 μL equivalent | Tirofiban | 20 | Solution | Transnasal | 10 |
| Comp. Ex. 34 | Tetanus toxoid-conjugated Haemophilus influenzae type b polysaccharide | Vaccine 100 μL equivalent | — | — | Solution | Sublingual | 30 |
| Ex. 147 | Tetanus toxoid-conjugated Haemophilus influenzae type b polysaccharide | Vaccine 100 μL equivalent | Argatroban | 100 | Solution | Sublingual | 30 |
| Ex. 148 | Tetanus toxoid-conjugated Haemophilus influenzae type b polysaccharide | Vaccine 100 μL equivalent | Nafamostat mesylate | 100 | Solution | Sublingual | 30 |
| Ex. 149 | Tetanus toxoid-conjugated Haemophilus influenzae type b polysaccharide | Vaccine 100 μL equivalent | Camostat mesylate | 100 | Solution | Sublingual | 30 |
| Ex. 150 | Tetanus toxoid-conjugated Haemophilus influenzae type b polysaccharide | Vaccine 100 μL equivalent | Tirofiban | 100 | Solution | Sublingual | 30 |
| Comp. Ex. 35 | Recombinant HBs antigen protein | Vaccine 100 μL equivalent | — | — | Solution | Transnasal | 10 |
| Ex. 151 | Recombinant HBs antigen protein | Vaccine 100 μL equivalent | Argatroban | 20 | Solution | Transnasal | 10 |
| Ex. 152 | Recombinant HBs antigen protein | Vaccine 100 μL equivalent | Nafamostat mesylate | 20 | Solution | Transnasal | 10 |
| Ex. 153 | Recombinant HBs antigen protein | Vaccine 100 μL equivalent | Camostat mesylate | 20 | Solution | Transnasal | 10 |
| Ex. 154 | Recombinant HBs antigen protein | Vaccine 100 μL equivalent | Tirofiban | 20 | Solution | Transnasal | 10 |
| Comp. Ex. 36 | Recombinant HBs antigen protein | Vaccine 100 μL equivalent | — | — | Solution | Sublingual | 30 |
| Ex. 155 | Recombinant HBs antigen protein | Vaccine 100 μL equivalent | Argatroban | 100 | Solution | Sublingual | 30 |
| Ex. 156 | Recombinant HBs antigen protein | Vaccine 100 μL equivalent | Nafamostat mesylate | 100 | Solution | Sublingual | 30 |
| Ex. 157 | Recombinant HBs antigen protein | Vaccine 100 μL equivalent | Camostat mesylate | 100 | Solution | Sublingual | 30 |
| Ex. 158 | Recombinant HBs antigen protein | Vaccine 100 μL equivalent | Tirofiban | 100 | Solution | Sublingual | 30 |
| Comp. Ex. 37 | Live attenuated yellow fever virus | Vaccine 100 μL equivalent | — | — | Solution | Transnasal | 10 |
| Ex. 159 | Live attenuated yellow fever virus | Vaccine 100 μL equivalent | Argatroban | 20 | Solution | Transnasal | 10 |
| Ex. 160 | Live attenuated yellow fever virus | Vaccine 100 μL equivalent | Nafamostat mesylate | 20 | Solution | Transnasal | 10 |
| Ex. 161 | Live attenuated yellow fever virus | Vaccine 100 μL equivalent | Camostat mesylate | 20 | Solution | Transnasal | 10 |
| Ex. 162 | Live attenuated yellow fever virus | Vaccine 100 μL equivalent | Tirofiban | 20 | Solution | Transnasal | 10 |
| Comp. Ex. 38 | Live attenuated yellow fever virus | Vaccine 100 μL equivalent | — | — | Solution | Sublingual | 30 |
| Ex. 163 | Live attenuated yellow fever virus | Vaccine 100 μL equivalent | Argatroban | 100 | Solution | Sublingual | 30 |

TABLE 10-continued

| | Antigen | | Immunity induction promoter | | | | |
|---|---|---|---|---|---|---|---|
| | Name | Amount [μg] | Name | Amount [μg] | Dosage form | Administration route | Amount [μL] |
| Ex. 164 | Live attenuated yellow fever virus | Vaccine 100 μL equivalent | Nafamostat mesylate | 100 | Solution | Sublingual | 30 |
| Ex. 165 | Live attenuated yellow fever virus | Vaccine 100 μL equivalent | Camostat mesylate | 100 | Solution | Sublingual | 30 |
| Ex. 166 | Live attenuated yellow fever virus | Vaccine 100 μL equivalent | Tirofiban | 100 | Solution | Sublingual | 30 |

TABLE 11

| | Antigen | | Immunity induction promoter | | | | |
|---|---|---|---|---|---|---|---|
| | Name | Amount [μg] | Name | Amount [μg] | Dosage form | Administration route | Amount [μL] |
| Comp. Ex. 39 | Tetanus toxoid | Vaccine 100 μL equivalent | — | — | Solution | Transnasal | 10 |
| Ex. 167 | Tetanus toxoid | Vaccine 100 μL equivalent | Argatroban | 20 | Solution | Transnasal | 10 |
| Ex. 168 | Tetanus toxoid | Vaccine 100 μL equivalent | Nafamostat mesylate | 20 | Solution | Transnasal | 10 |
| Ex. 169 | Tetanus toxoid | Vaccine 100 μL equivalent | Camostat mesylate | 20 | Solution | Transnasal | 10 |
| Ex. 170 | Tetanus toxoid | Vaccine 100 μL equivalent | Tirofiban | 20 | Solution | Transnasal | 10 |
| Comp. Ex. 40 | Tetanus toxoid | Vaccine 100 μL equivalent | — | — | Solution | Sublingual | 30 |
| Ex. 171 | Tetanus toxoid | Vaccine 100 μL equivalent | Argatroban | 100 | Solution | Sublingual | 30 |
| Ex. 172 | Tetanus toxoid | Vaccine 100 μL equivalent | Nafamostat mesylate | 100 | Solution | Sublingual | 30 |
| Ex. 173 | Tetanus toxoid | Vaccine 100 μL equivalent | Camostat mesylate | 100 | Solution | Sublingual | 30 |
| Ex. 174 | Tetanus toxoid | Vaccine 100 μL equivalent | Tirofiban | 100 | Solution | Sublingual | 30 |
| Comp. Ex. 41 | Live attenuated varicella virus | Vaccine 100 μL equivalent | — | — | Solution | Transnasal | 10 |
| Ex. 175 | Live attenuated varicella virus | Vaccine 100 μL equivalent | Argatroban | 20 | Solution | Transnasal | 10 |
| Ex. 176 | Live attenuated varicella virus | Vaccine 100 μL equivalent | Nafamostat mesylate | 20 | Solution | Transnasal | 10 |
| Ex. 177 | Live attenuated varicella virus | Vaccine 100 μL equivalent | Camostat mesylate | 20 | Solution | Transnasal | 10 |
| Ex. 178 | Live attenuated varicella virus | Vaccine 100 μL equivalent | Tirofiban | 20 | Solution | Transnasal | 10 |
| Comp. Ex. 42 | Live attenuated varicella virus | Vaccine 100 μL equivalent | — | — | Solution | Sublingual | 30 |
| Ex. 179 | Live attenuated varicella virus | Vaccine 100 μL equivalent | Argatroban | 100 | Solution | Sublingual | 30 |
| Ex. 180 | Live attenuated varicella virus | Vaccine 100 μL equivalent | Nafamostat mesylate | 100 | Solution | Sublingual | 30 |
| Ex. 181 | Live attenuated varicella virus | Vaccine 100 μL equivalent | Camostat mesylate | 100 | Solution | Sublingual | 30 |
| Ex. 182 | Live attenuated varicella virus | Vaccine 100 μL equivalent | Tirofiban | 100 | Solution | Sublingual | 30 |
| Comp. Ex. 43 | Live BCG | Vaccine 30 μL equivalent | — | — | Solution | Transnasal | 10 |
| Ex. 183 | Live BCG | Vaccine 30 μL equivalent | Argatroban | 20 | Solution | Transnasal | 10 |
| Ex. 184 | Live BCG | Vaccine 30 μL equivalent | Nafamostat mesylate | 20 | Solution | Transnasal | 10 |
| Ex. 185 | Live BCG | Vaccine 30 μL equivalent | Camostat mesylate | 20 | Solution | Transnasal | 10 |
| Ex. 186 | Live BCG | Vaccine 30 μL equivalent | Tirofiban | 20 | Solution | Transnasal | 10 |
| Comp. Ex. 44 | Live BCG | Vaccine 30 μL equivalent | — | — | Solution | Sublingual | 30 |
| Ex. 187 | Live BCG | Vaccine 30 μL equivalent | Argatroban | 100 | Solution | Sublingual | 30 |
| Ex. 188 | Live BCG | Vaccine 30 μL equivalent | Nafamostat mesylate | 100 | Solution | Sublingual | 30 |
| Ex. 189 | Live BCG | Vaccine 30 μL equivalent | Camostat mesylate | 100 | Solution | Sublingual | 30 |
| Ex. 190 | Live BCG | Vaccine 30 μL equivalent | Tirofiban | 100 | Solution | Sublingual | 30 |
| Comp. Ex. 45 | Inactivated rabies virus | Vaccine 200 μL equivalent | — | — | Solution | Transnasal | 10 |
| Ex. 191 | Inactivated rabies virus | Vaccine 200 μL equivalent | Argatroban | 20 | Solution | Transnasal | 10 |
| Ex. 192 | Inactivated rabies virus | Vaccine 200 μL equivalent | Nafamostat mesylate | 20 | Solution | Transnasal | 10 |
| Ex. 193 | Inactivated rabies virus | Vaccine 200 μL equivalent | Camostat mesylate | 20 | Solution | Transnasal | 10 |
| Ex. 194 | Inactivated rabies virus | Vaccine 200 μL equivalent | Tirofiban | 20 | Solution | Transnasal | 10 |
| Comp. Ex. 46 | Inactivated rabies virus | Vaccine 200 μL equivalent | — | — | Solution | Sublingual | 30 |
| Ex. 195 | Inactivated rabies virus | Vaccine 200 μL equivalent | Argatroban | 100 | Solution | Sublingual | 30 |
| Ex. 196 | Inactivated rabies virus | Vaccine 200 μL equivalent | Nafamostat mesylate | 100 | Solution | Sublingual | 30 |
| Ex. 197 | Inactivated rabies virus | Vaccine 200 μL equivalent | Camostat mesylate | 100 | Solution | Sublingual | 30 |
| Ex. 198 | Inactivated rabies virus | Vaccine 200 μL equivalent | Tirofiban | 100 | Solution | Sublingual | 30 |

EXAMPLES 199 to 203, Comparative Example 47

A cream for transdermal administration was prepared according to the formulation shown in Table 12 in the same manner as the cream for transdermal administration of Table 5. The right back of a mouse (C57BL6 NCr mouse, female, 7 weeks old) was shaved, and after the skin was subjected to a corneum removing treatment five times with an OPP tape (EZ Dunplon No. 3301EZ, Nitto Denko Corporation), the cream was administered to the skin (minimally invasive administration), and the left back was shaved at the same time. Twenty-four hours later, the cream for transdermal administration on the right back was removed. One week after the administration, the skin of the left back of the mouse was subjected to a corneum removing treatment in the same manner as above, and the cream for transdermal administration was administered thereto. The cream was removed 24 hours later. One week after the second administration, the mouse serum was taken, and the antigen (OVA)-specific IgG antibody in the serum was determined by ELISA. Also in the immunization using the minimally invasive administration, humoral immunity specific to the administered antigen can be induced.

TABLE 12

| No. | Administration route | Dosage form | Antigen Name | Antigen Amount [Parts by weight] | Immunity induction promoter Name | Immunity induction promoter Amount [Parts by weight] | Immunological evaluation mouse |
|---|---|---|---|---|---|---|---|
| Comp. Ex. 47 | Transdermal (minimally invasive) | Cream | OVA | 5 | — | — | C57BL6 |
| Ex. 199 | Transdermal (minimally invasive) | Cream | OVA | 5 | Rivaroxaban | 5 | C57BL6 |
| Ex. 200 | Transdermal (minimally invasive) | Cream | OVA | 5 | Argatroban | 5 | C57BL6 |
| Ex. 201 | Transdermal (minimally invasive) | Cream | OVA | 5 | Nafamostat mesylate | 5 | C57BL6 |
| Ex. 202 | Transdermal (minimally invasive) | Cream | OVA | 5 | Camostat mesylate | 5 | C57BL6 |
| Ex. 203 | Transdermal (minimally invasive) | Cream | OVA | 5 | Tirofiban | 5 | C57BL6 |

INDUSTRIAL APPLICABILITY

The humoral immunity induction-promoting composition and vaccine pharmaceutical composition of the present invention can universally be used for inducing humoral immunity to various antigens, exert a high antibody production inducing effect, and can be suitably used for transdermal administration or transmucosal administration.

The invention claimed is:

1. A vaccine pharmaceutical composition for inducing humoral immunity, comprising:

an infectious pathogen-derived antigen in an amount of 0.000001 to 50% by weight based on a total weight of the vaccine pharmaceutical composition; and a humoral immunity induction-promoting composition comprising a humoral immunity induction promoter whose active ingredient is a thrombosis treatment drug, wherein the humoral immunity induction promoter is present in an amount of 0.001 to 10,000 parts by weight based on 1 part by weight of the antigen;

wherein the infectious pathogen is selected from adenovirus, herpesvirus, picornavirus, poxvirus, picornavirus, orthomyxovirus, paramyxovirus, parvovirus, togavirus, coronavirus, hepadnavirus, flavivirus, hepevirus, papillomavirus, calicivirus, rhabdovirus, filovirus, arenavirus, bunyavirus, reovirus, retrovirus, Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococci, Clostridium, Bacillus, Corynebacterium, Mycobacterium, Campyrobacter, Vibrio, Serratia, Providencia, Chromobacterium, Brucella, Yersinia, Haemophilus, Bordetella, and pathogens that cause chlamydia, candidiasis, aspergillosis, histoplasmosis, cryptococcal meningitis, malaria, pneumocystis carinii pneumonia, leishmaniasis, cryptosporidiosis, toxoplasmosis, and Trypanosoma infection; and wherein the thrombosis treatment drug is a thrombogenesis-suppressing compound that is at least one of an anticoagulant or an antiplatelet, the anticoagulant being at least one selected from the group consisting of fondaparinux, rivaroxaban, apixaban, edoxaban, betrixaban, eribaxaban, ximelagatran, dabigatran, argatroban, hirudin, nafamostat, camostat, gabexate, and warfarin, and the antiplatelet being at least one selected from the group consisting of abciximab, eptifibatide, and tirofiban.

2. The vaccine pharmaceutical composition according to claim 1, wherein the composition is formulated to be administered to a body surface.

3. The vaccine pharmaceutical composition according to claim 1, wherein the composition is formulated to be administered by intradermal injection, subcutaneous injection, or intramuscular injection.

4. The vaccine pharmaceutical composition according to claim 1, wherein the infectious pathogen is influenza.

5. The vaccine pharmaceutical composition according to claim 1, wherein the infectious pathogen-derived antigen is selected from H1N1, H3N2, Influenza B virus, Influenza B virus, pneumococcal capsular polysaccharide, HPV16 recombinant protein, live attenuated rotavirus, inactivated poliovirus, inactivated hepatitis A virus, inactivated Japanese encephalitis virus, live attenuated mumps virus, live attenuated measles virus, live attenuated rubella virus, tetanus toxoid-conjugated haemophilus influenzae type b polysaccharide, recombinant HBs antigen protein, live attenuated yellow fever virus, tetanus toxoid, live attenuated varicella virus, live BCG, and inactivated rabies virus.

6. The vaccine pharmaceutical composition according to claim 5, wherein the thrombosis treatment drug is selected from argatroban, nafamostat mesylate, camostat mesylate, and tirofiban.

7. A vaccine pharmaceutical composition for inducing humoral immunity, comprising:

an infectious pathogen-derived antigen; and a humoral immunity induction-promoting composition comprising argatroban.

* * * * *